United States Patent
Ulric et al.

(10) Patent No.: US 9,623,267 B2
(45) Date of Patent: *Apr. 18, 2017

(54) ULTRASONIC TREATMENT OF ADIPOSE TISSUE AT MULTIPLE DEPTHS

(75) Inventors: Tanar Ulric, Woodinville, WA (US); Charles S. Desilets, Mukilteo, WA (US); Blake Little, Bothell, WA (US)

(73) Assignee: LIPOSONIX, INC., Bothell, WA (US)

( * ) Notice: Subject to any disclaimer, the term of this patent is extended or adjusted under 35 U.S.C. 154(b) by 1714 days.

This patent is subject to a terminal disclaimer.

(21) Appl. No.: 12/717,818

(22) Filed: Mar. 4, 2010

(65) Prior Publication Data

US 2010/0249669 A1  Sep. 30, 2010

Related U.S. Application Data

(60) Provisional application No. 61/157,534, filed on Mar. 4, 2009.

(51) Int. Cl.
| | | |
|---|---|---|
| *A61H 1/00* | (2006.01) | |
| *A61N 7/02* | (2006.01) | |
| *A61N 7/00* | (2006.01) | |
| *A61B 34/30* | (2016.01) | |

(52) U.S. Cl.
CPC ............ *A61N 7/02* (2013.01); *A61B 34/30* (2016.02); *A61N 2007/0008* (2013.01); *A61N 2007/0082* (2013.01); *A61N 2007/0091* (2013.01); *A61N 2007/0095* (2013.01)

(58) Field of Classification Search
CPC .................................. A61N 7/02; A61N 7/00
USPC ........................................................ 601/3
See application file for complete search history.

(56) References Cited

U.S. PATENT DOCUMENTS

| | | | |
|---|---|---|---|
| 5,873,902 A * | 2/1999 | Sanghvi et al. | 607/96 |
| 6,325,769 B1 | 12/2001 | Klopotek | |
| 8,282,554 B2 | 10/2012 | Makin et al. | |
| 2005/0154332 A1* | 7/2005 | Zanelli et al. | 601/2 |
| 2005/0187495 A1* | 8/2005 | Quistgaard et al. | 601/2 |

(Continued)

FOREIGN PATENT DOCUMENTS

| | | |
|---|---|---|
| JP | 2004358624 A | 12/2004 |
| JP | 2006223877 A | 8/2006 |

(Continued)

OTHER PUBLICATIONS

Office Action issued in counterpart European Application No. 10 708 063.2 on Aug. 23, 2012 (5 pages).

(Continued)

*Primary Examiner* — Tse Chen
*Assistant Examiner* — Hien Nguyen
(74) *Attorney, Agent, or Firm* — Thompson Hine LLP

(57) ABSTRACT

Methods and apparatus (100) are described for modifying unwanted tissue for cosmetic reasons. The methods provide a non-invasive manner to perform body contouring by destroying adipose tissue while simultaneously causing collagen contraction in a single procedure. Adipose tissue destroyed during the medical procedure may be removed from a treatment volume during the wound healing process, allowing the treatment volume to gradually shrink (22). The gradual shrinkage may promote better skin tone in the treatment area. The procedure may involve multiple treatments to the same treatment area or location.

35 Claims, 26 Drawing Sheets

(56) References Cited

U.S. PATENT DOCUMENTS

2006/0122509 A1   6/2006  Desilets
2007/0055156 A1*  3/2007  Desilets et al. ............... 600/439
2007/0219448 A1*  9/2007  Seip et al. .................... 600/454

FOREIGN PATENT DOCUMENTS

| JP | 2007516806 A | 6/2007 |
|---|---|---|
| JP | 2008513128 A | 5/2008 |
| JP | 2008515557 A | 5/2008 |
| JP | 2008539037 A | 11/2008 |
| JP | 2009011584 A | 1/2009 |
| WO | WO 2005/011804 A2 | 2/2005 |
| WO | 2006137484 A1 | 12/2006 |
| WO | 2008144274 A2 | 11/2008 |
| WO | WO 2008/144724 A2 | 11/2008 |

OTHER PUBLICATIONS

Office Action issued in counterpart Korean Patent Application No. 2011-7020725 on Nov. 12, 2012 (4 pages—English translation only).

Instituto Mexicano de la Propiedad Industrial, Office Action issued in Mexican Patent Application No. MX/a/2011/009217 dated Sep. 20, 2013.

Patent Office of the Russian Federation, Office Action received in related Russian patent application No. 2011140174 dated Dec. 19, 2012.

Japan Patent Office, Office Action issued in Japanese Patent Application No. 2011-553113 dated Apr. 11, 2013 and translation thereto.

Ukrainian Patent Office, Office Action issued in Ukrainian application No. 201111677 dated May 3, 2013.

\* cited by examiner

| Motion Table Entry Description | Value(s) |
|---|---|
| X Geometry Type | Line |
| X Entry 1 | XStart, XStop, XVelocity |
| ... | |
| X Entry n | XStart, XStop, XVelocity |
| Y Geometry Type | Line |
| Y Entry 1 | YStart, YStop, YVelocity |
| ... | |
| Y Entry n | YStart, YStop, YVelocity |
| Z Geometry Type | Sinusoidal |
| Z Entry 1 | Frequency, Magnitude |
| ... | |
| Z Entry n | Frequency, Magnitude |

FIG. 23

| Motion Table Entry Description | Value(s) |
|---|---|
| X Geometry Type | Line |
| X Entry 1 | XStart = -6, XStop=-6, XVelocity=18 |
| X Entry 2 | XStart = -6, XStop=-2, XVelocity=18 |
| X Entry 3 | XStart = -2, XStop=-2, XVelocity=18 |
| X Entry 4 | XStart = -2, XStop= 2, XVelocity=18 |
| X Entry 5 | XStart = 2, XStop= 2, XVelocity=18 |
| X Entry 6 | XStart = 2, XStop= 6, XVelocity=18 |
| X Entry 7 | XStart = 6, XStop= 6, XVelocity=18 |
| Y Geometry Type | Line |
| Y Entry 1 | YStart = -6, XStop= 6, XVelocity=18 |
| Y Entry 2 | YStart = 6, XStop= 6, XVelocity=18 |
| Y Entry 3 | YStart = 6, XStop=-6, XVelocity=18 |
| Y Entry 4 | YStart = -6, XStop= -6, XVelocity=18 |
| Y Entry 5 | YStart = -6, XStop= 6, XVelocity=18 |
| Y Entry 6 | YStart = 6, XStop= 6, XVelocity=18 |
| Y Entry 7 | YStart = 6, XStop=-6, XVelocity=18 |
| Z Geometry Type | Sinusoidal |
| Z Entry1 | Frequency = 15Hz, Magnitude=1mm |
| Z Entry2 | Frequency = 15Hz, Magnitude=1mm |
| Z Entry3 | Frequency = 15Hz, Magnitude=1mm |
| Z Entry4 | Frequency = 15Hz, Magnitude=1mm |
| Z Entry5 | Frequency = 15Hz, Magnitude=1mm |
| Z Entry6 | Frequency = 15Hz, Magnitude=1mm |
| Z Entry7 | Frequency = 15Hz, Magnitude=1mm |

FIG. 24

ULTRASONIC TREATMENT OF ADIPOSE TISSUE AT MULTIPLE DEPTHS

CROSS-REFERENCES TO RELATED APPLICATIONS

This application claims the benefit of U.S. Provisional Patent Application 61/157,534 filed Mar. 4, 2009, the full disclosure of which is incorporated herein by reference.

BACKGROUND

1. Field of the Invention

The present invention relates to using ultrasound apparatus and methods for the noninvasive modification of adipose tissue.

2. Description of the Prior Art

Body sculpting has developed into a highly sought after procedure for restoring people to a leaner, trimmer physique. The field of cosmetic surgery has ballooned considerably with developments in both tools and techniques. One of the more popular for quick body sculpting is liposuction.

More recently systems and methods have been developed for the noninvasive destruction of adipose tissue. These systems utilize separately or in combination high intensity focused ultrasound (HIFU), radio frequency (RF) or lasers. These systems utilize one or more energy forms to penetrate the skin and effect the adipose tissue below. Systems vary in their desired effect to the selective destruction of adipose tissue without harming other tissue, to generally destruction of adipose tissue and non-adipose structures within the same vicinity.

BRIEF SUMMARY

The following presents a simplified summary of some embodiments of the invention in order to provide a basic understanding of the invention. This summary is not an extensive overview of the invention. It is not intended to identify key/critical elements of the invention or to delineate the scope of the invention. Its sole purpose is to present some embodiments of the invention in a simplified form as a prelude to the more detailed description that is presented later.

In an embodiment, there are methods of modifying adipose tissue using high intensity focused ultrasound. The method involves determining a volume of adipose tissue to be treated, identifying a corresponding surface area of skin over the volume of adipose tissue, moving a HIFU therapy transducer on the surface area of skin and applying multiple treatments of therapeutic ultrasound energy into the volume of adipose tissue such that a number of necrosed tissue cells and denatured collagen fibrils are produced.

In another embodiment, there are methods of reducing adipose tissue volume in a patient using high intensity focused ultrasound. The method involves determining a volume of adipose tissue to be treated, identifying a corresponding surface area of skin over the volume of adipose tissue and applying multiple treatments of high intensity focused ultrasound energy to the area in a manner sufficient to induce the gradual destruction of said adipose tissue and denaturing of collagen fibrils, the energy flux being of at least 35 J/cm$^2$.

In another embodiment, there is a medical ultrasound therapy system. The system has a therapy head including at least one high intensity focused ultrasound transducer. The system also has a controller which includes a data store storing information about a three dimensional treatment profile for the therapy head and a processor coupled to the data store, the processor generates a three dimensional treatment cycle for the therapy head in accordance with the information, the three dimensional treatment cycle includes treatments by the therapy head at a variety of different depths.

In an aspect of the system of the invention, the therapy head may include an enclosure with a partition, the partition defining a first and second chamber within the enclosure, a motor assembly may be within the first chamber and fluid within the second chamber. The high intensity focused ultrasound transducer may be movable within the second chamber through motor command provided to the motor assembly from the controller.

In another embodiment the data store may contain information stored in library tables. The data store may also contain profile data particular to various anatomical regions of adipose tissue. The profile data may be adapted for gender variations.

In an embodiment, the therapy head may be adapted for various anatomical regions of adipose tissue.

In an embodiment, the controller may be adapted to promote an effect of necrosis of adipose tissue and/or to promote an effect of denaturing collagen fibrils.

In another embodiment there is a medical ultrasound therapy system having a therapy head including at least one high intensity focused ultrasound transducer, a controller for generating a three dimensional treatment plan for the therapy head. The controller includes a data access component for accessing data defining a three dimensional treatment profile for a treatment of a defined region of a patient. The treatment profile may include information about treatments to be conducted at several different depths. The system also includes a treatment plan component for generating a treatment plan based upon the treatment profile. The treatment plan including treatments defined for the therapy head at the several different depths in accordance with the information.

In an aspect of the system of the invention, the therapy head may include an enclosure with a partition, the partition defining a first and second chamber within the enclosure. There can be a motor assembly within the first chamber and fluid in the second chamber. The high intensity focused ultrasound transducer may be movable within the second chamber through motor command provided to the motor assembly from the controller. The therapy head may be adapted for various anatomical regions of adipose tissue.

The data store of the system may include information stored in library tables and/or profile data particular to various anatomical regions of adipose tissue. The profile data may be adapted for gender variations.

In an embodiment, the controller may be adapted to promote an effect of necrosis of adipose tissue and/or promote an effect of denaturing collagen fibrils.

In another embodiment, there are methods for treating a patient with high intensity focused ultrasound involving positioning a therapy head having at least one high intensity focused ultrasound transducer against a first location on a patient, and using an automated process while at the first location, ablating tissue with the transducer at a first depth then while at the first location, ablating tissue with the transducer at a second depth.

The automated process may include accessing information about multiple depth profiles for the therapy head and generating a multi-depth treatment cycle for the therapy head in accordance with the information, the multi-depth treatment cycle including treatments by the therapy head at a variety of depths.

In an aspect of the methods described, the information may be stored in library tables. The information may be profile data particular to various anatomical regions of adipose tissue. The profile data may be adapted for gender variations.

In an aspect of the methods described, the therapy head may include an enclosure with a partition, the partition defining a first and second chamber within the enclosure. A motor assembly may be positioned in the first chamber and fluid within the second chamber. The high intensity focused ultrasound transducer may be movable within the second chamber through motor command provided to the motor assembly from the controller. The automated process involves the ultrasound transducer moving within the second chamber through motor command. Depth variation may be provided by varying the focus of the ultrasound transducer. Ablating tissue may involve promoting an effect of necrosis of adipose tissue and/or promoting promote an effect of denaturing collagen fibrils.

In another embodiment, there are medical ultrasound therapy systems including a therapy head including at least one high intensity focused ultrasound transducer and a controller. The controller may include a data store, having stored thereon a data structure, the data structure may include a tissue ablation treatment routine having a first data field containing data representing a routine for first ablation of tissue at a first depth in accordance with the routine and a second data field representing a routine for second ablation of tissue at a second depth in accordance with the routine. The controller can include a processor coupled to the data store, the processor accessing the data structure and instructing the therapy head to perform the routine in an automated process and including the first ablation and the second ablation.

In an aspect of the systems described, the therapy head may include an enclosure with a partition, the partition defining a first and second chamber within the enclosure. A motor assembly may be positioned within the first chamber and fluid within the second chamber. The high intensity focused ultrasound transducer may be movable within the second chamber through motor command provided to the motor assembly from the controller.

In another aspect, the system may include a data store having information stored in library tables. The data store may include profile data particular to various anatomical regions of adipose tissue. The profile data may be adapted for gender variations.

In an embodiment, the systems can include therapy heads that may be adapted for various anatomical regions of adipose tissue. Alternatively or in addition, the controller may be adapted to promote an effect of necrosis of adipose tissue and or promote an effect of denaturing collagen fibrils.

BRIEF DESCRIPTION OF THE DRAWINGS

FIGS. 23 and 24 provide example tables for the data store.

DETAILED DESCRIPTION OF THE INVENTION

Figure 1:
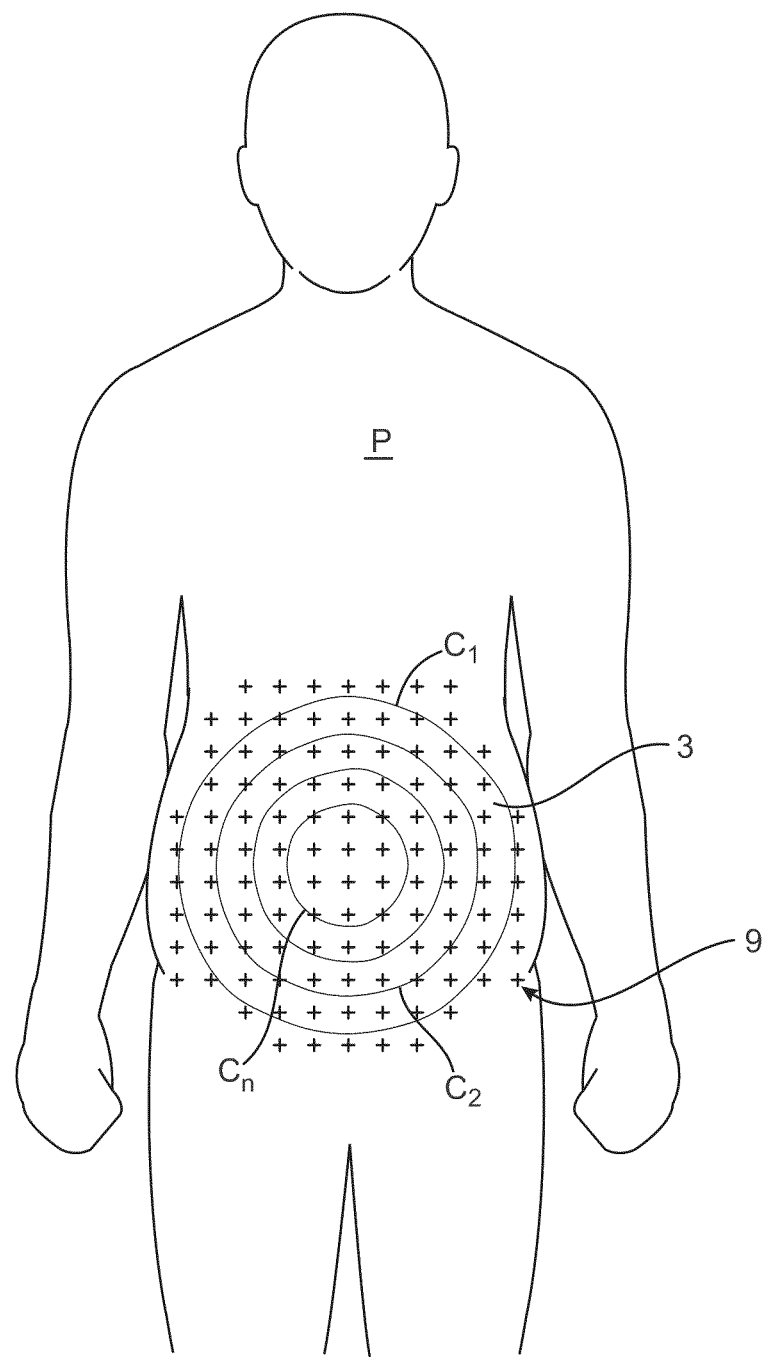
FIG. 1 shows contour and gridlines on a patient.

It should be understood on reviewing the present disclosure that the figures and drawing provided herein are illustrations only. Items shown in these drawings are not intended to be to scale with respect to any key or legend, nor to scale within each drawing. The illustrations may exaggerate particular elements expressly for the purpose of illustrating the element and assisting in the understanding of the accompanying specification.

Methods to address the various issues of patient concern when looking for a non-invasive alternative to liposuction are now described. In an embodiment there can be a method of modifying tissue using high intensity focused ultrasound. The method comprises the steps of determining a volume of adipose tissue to be treated, identifying a corresponding surface area of skin over the volume of adipose tissue; and moving a HIFU therapy transducer on the surface area of skin, and applying therapeutic ultrasound energy into the volume of adipose tissue so that a plurality of cells or pockets, of tissue necroses and denatured collagen fibrils are produced.

Determining a volume of adipose tissue to be treated may be similar to the pretreatment procedures used by cosmetic surgeons prior to a liposuction procedure. A manual pinch test or caliper test can be used by a trained physician to determine if a patient has sufficient adipose tissue at a particular site to warrant a liposuction procedure. The safety measure and standard used by such a test can also satisfy the minimum requirements of a HIFU procedure such as described herein. Alternatively, a physician may use an imaging instrument such as a diagnostic ultrasound device, an MRI device, or a simple A-line scanner to determine if there is sufficient adipose tissue depth in a desired area to be treated using HIFU energy.

While the depth of the adipose tissue should be sufficient to allow the focal zone of the HIFU transducer to be safely in the adipose tissue with some margin of safety both above and below the focal point of the transducer, it should be understood that varying the focal depth of the transducer, as well as the shape and focus of the transducer can allow for more precise control over the delivery of HIFU energy, while simultaneously reducing the clearance zones needed for safe operation. That is to say a highly focused transducer should provide sufficient control and focus to allow for a reduced safety clearance.

Once the volume of tissue is identified, the physician may determine the corresponding surface area over the volume that can be treated. Once again, borrowing from existing techniques in liposuction, the physician may proceed directly to treating the patient using a HIFU transducer, or she can create one or more contour lines as part of the treatment planning phase of an ordinary liposuction procedure. During this step the physician may draw or otherwise indicate on a patient skin surface, a region that can safely be treated using a HIFU transducer. Pens or markers may be used to create these contour lines.

Next is the application of HIFU energy into the volume of adipose tissue. In an embodiment, a HIFU transducer is moved over the surface area identified above. The transducer emits energy to the focal zone in sufficient strength (power) and intensity (pressure) to cause cellular necrosis and collagen fibril denaturing. Depending on the pulse repetition frequency and velocity that the transducer is moving, a plurality of discrete treatment cells may be produced. Each treatment cell absorbs sufficient energy from the transducer to cause cellular necrosis of cells in the focal zone, as well as collagen denaturing in the same region. The volume of tissue affected at the focal zone of the transducer is the lesion field 630 (FIGS. 3A-3D, 4A-4C, 5A-5B). The volume around the lesion field 630 where adipose tissue is destroyed and/or collagen fibrils are denatured is the halo field 6. If the transducer is moved in a continuous manner such that a single linear lesion field is formed along the path or axis of motion, the lesion field is said to be contiguous, or a contiguous lesion field 630*c*. Similarly the halo field 6 may be a contiguous halo field 6*c*. A volume of over lapping lesion field produced from more than one scan line (such as an intersection) forms a cooperative lesion field, while overlapping halo fields are referred to as cooperative halo fields. Overlapping halo fields may be produced by operating the HIFU transducer in a manner such that scan lines intersect one another, or run parallel close enough so their corresponding halo zones overlap. The sum of the tissue volume of the various lesion fields and halo fields produced during a therapy procedure comprises the treatment area 3.

In accordance with an embodiment, the application of HIFU energy into the volume of adipose energy may involve multiple treatments at the same location. In such an embodiment, the cumulative strength (power) and intensity (pressure) may be sufficient to cause cellular necrosis and collagen fibril denaturing. This cumulative effect permits each individual treatment to be of insufficient power and intensity to cause cellular necrosis and collagen fibril denaturing.

Figure 14:
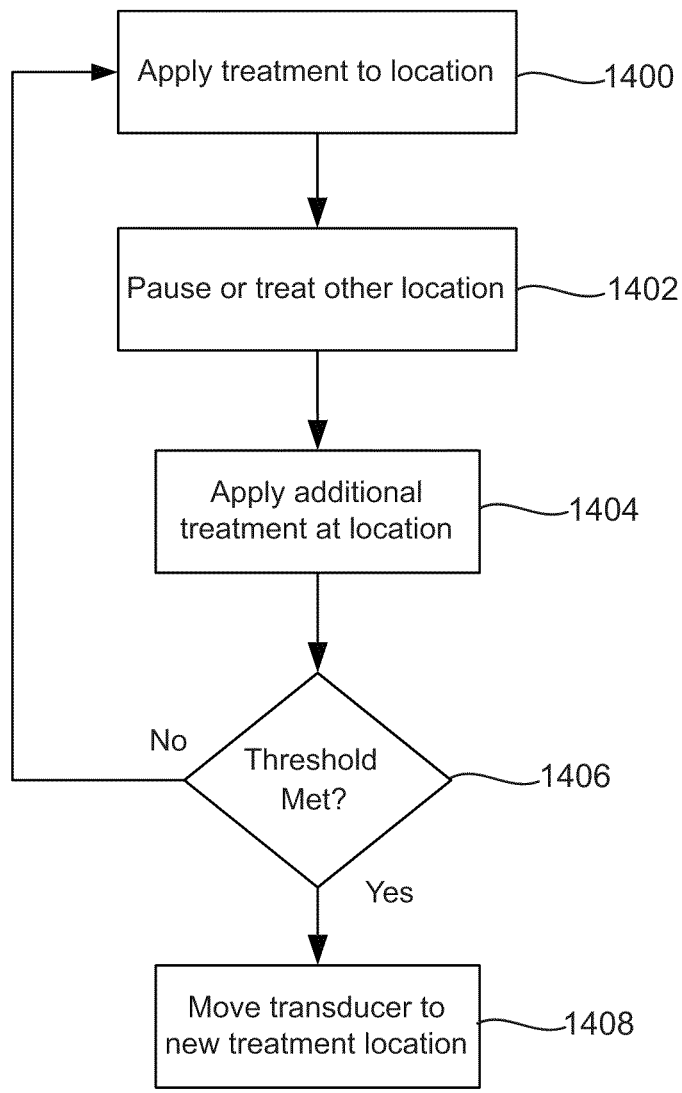
FIG. 14 is a flow chart showing steps for providing multiple treatments to a single location in accordance with an embodiment.

FIG. 14 is a flow chart showing steps for providing multiple treatments to a single location in accordance with an embodiment. Beginning at step 1400, a first application of HIFU energy (i.e., a first treatment) may be applied into a particular location in adipose tissue. At step 1402, a pause may be taken, during which treatment may be applied to another location. At step 1404, an additional treatment may be applied to the same location. At step 1406, a determination may be made whether the power of the cumulative treatments is sufficient to cause cellular necrosis and collagen fibril denaturing. If not, the process branches back to step 1400, and a further treatment may be applied. If so, the applications at that location may be completed.

It may be understood that such cumulative treatments may be repeated to accumulate even more power, but at a minimum, the accumulation may be sufficient to cause cellular necrosis and collagen fibril denaturing. Also, an evaluation need not be done after each treatment (as indicated by step 1406), but instead the number of treatments at a given location may be determined empirically or clinically. It should also be understood that the application of energy to the treatment site may vary from one treatment to another at the same location. For instance, in an aspect of the system and/or methods of the invention, ultrasound may be applied at value of X power and/or pressure to a region of tissue, it may be applied in more than one application in which all applications are equal, or in which the sum of the applications is X, but each application may be a different fraction of X (either in equal fractions, or variable fractions that sum to X). Once the desired application of energy is achieved, the transducer may be relocated to a new location and the process may be repeated at a different location at step 1408.

The destruction of adipose tissue in the lesion field is not restricted to adipocytes (fat cells) alone. The methods described herein are intended to destroy biological tissue within the focal zone by whatever mechanism the HIFU transducer can produce. Furthermore the thermal energy which radiates from the lesion field destroys the surrounding tissue forming the halo field. This thermal radiation is not intended to be of a particular temperature for selective preservation of any biological material. The temperature in the halo field should be sufficient to destroy the adipose tissue and denature the collagen fibrils. Thus, it may be possible that other cells or tissue types within the lesion and halo field will be destroyed.

Figure 11:
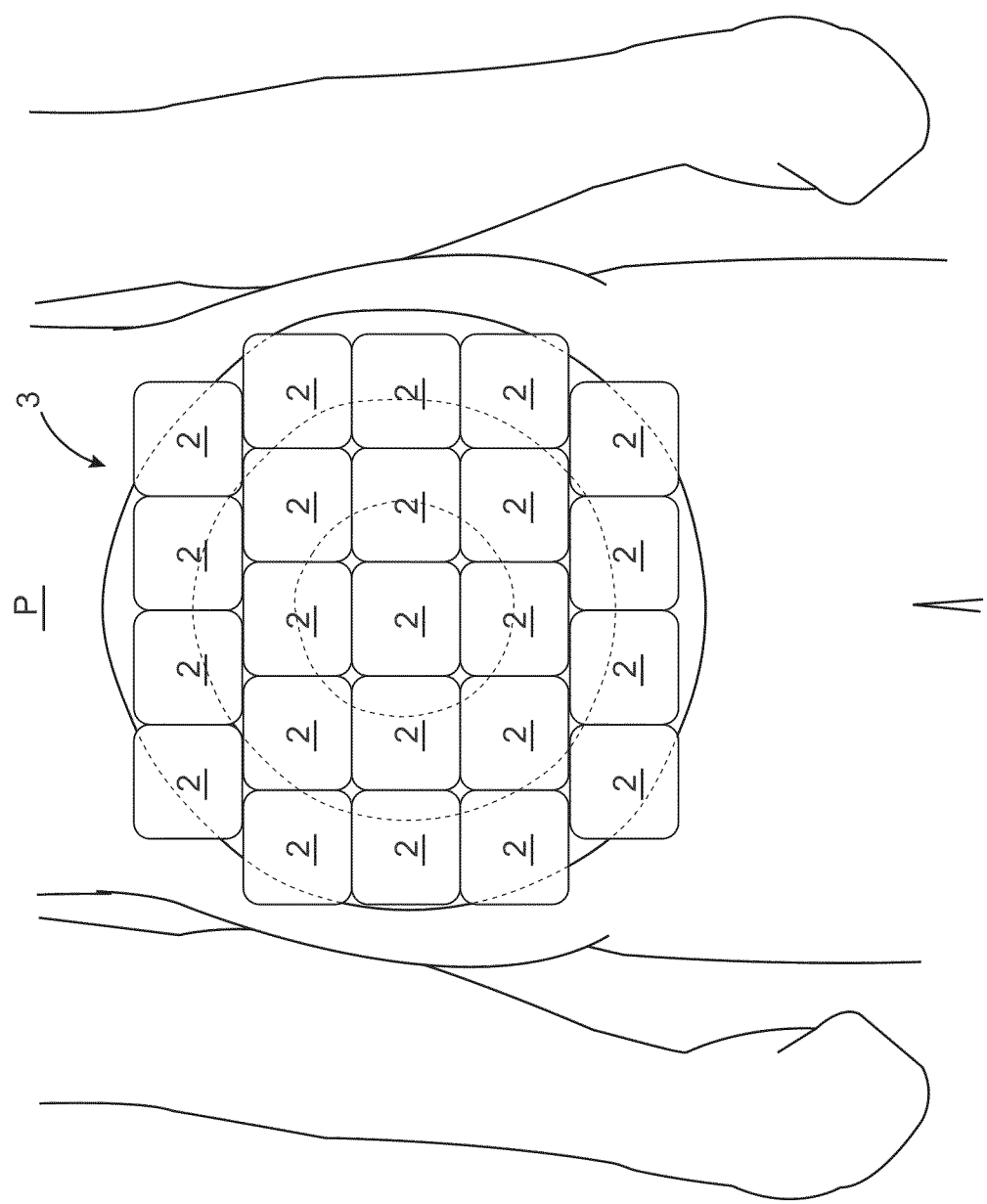
FIG. 11 shows a mosaic of treatment sites used to cover a treatment area.

In an embodiment, the application of HIFU energy may be done in a manner to form a pattern of discrete lesion fields 630 and halo fields 6 within a treatment area 3. In another embodiment, the application of HIFU may be done in a manner that divides the treatment area 3 into a plurality of smaller treatment sites 2, and the sum of the treatment sites 2 produces the desired coverage to form the treatment area 3 (FIG. 11). Alternatively, HIFU energy may be applied in either continuous or discontinuous motion through individual treatment sites 2, or across the entire treatment zone 3. The various treatment sites 2 which form the treatment zone 3 on a patient may be uniform or different in both size of each treatment site 2 within the treatment zone 3, as well as having any mixture of lesion fields 630, contiguous lesion fields 630*c*, cooperative lesion fields, halo fields 6, contiguous halo fields and cooperative halo fields. In addition, for each treatment site, as described herein, multiple treatments may be provided, with the multiple treatments having any of these forms.

Figure 8:
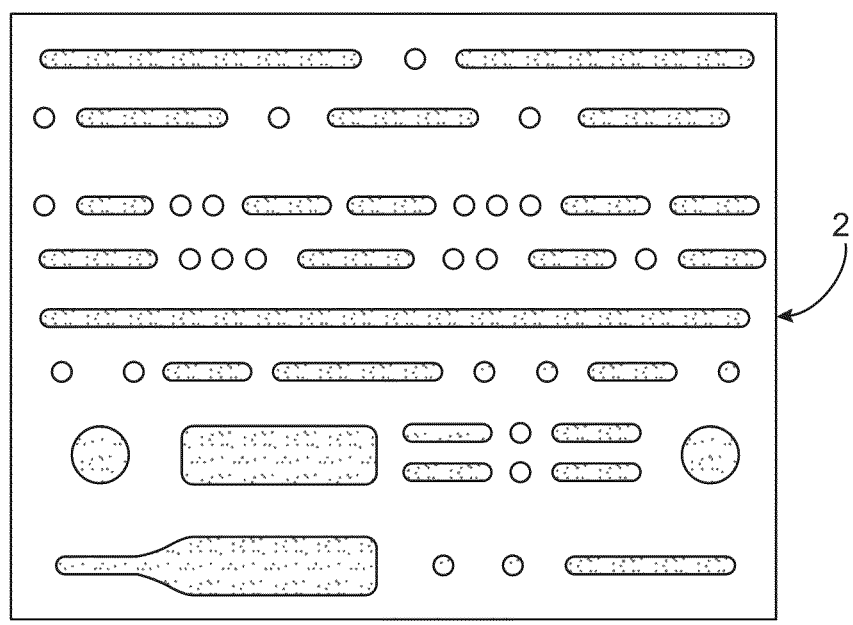

In yet another embodiment of ultrasound application according to the present methods, the transducer may be used to deposit energy and produce lesion fields of varying shapes and sizes. If the transducer resides in a single position (such as using an incremental movement), the transducer may initially create a small lesion field. By allowing the transducer to loiter, thermal energy will build up and radiate out from the lesion field. The transducer may be moved slowly or have higher energy output while moved in a regular movement pattern to produce larger contiguous lesion fields (produce thicker scan lines). By analogy, one may envision the way a fountain pen leaves ink on a page. Just as the nib of a fountain pen allows ink to spread across paper from the point of contact of the nib, so to does thermal energy radiate out from the focal zone of the transducer the longer the transducer is left to loiter over a particular spot of adipose tissue. Some variations of these lesions are shown in FIG. 8. Similar to those scan lines 4, lesion fields 630 and halo field 6 previously described, there are now shown enlarged halo fields. Here the scan line 4 may produce a spot shaped lesion field 630 with a generally spherical shaped halo field 6. Increasing the power broadcast into the tissue may be achieved by moving the transducer slowly, varying the parameters of the transducer, so that more energy radiates from the lesion field into the surrounding tissue, thus producing an enlarged halo field. Similarly, the lesion field itself may also increase in size.

Figure 15:
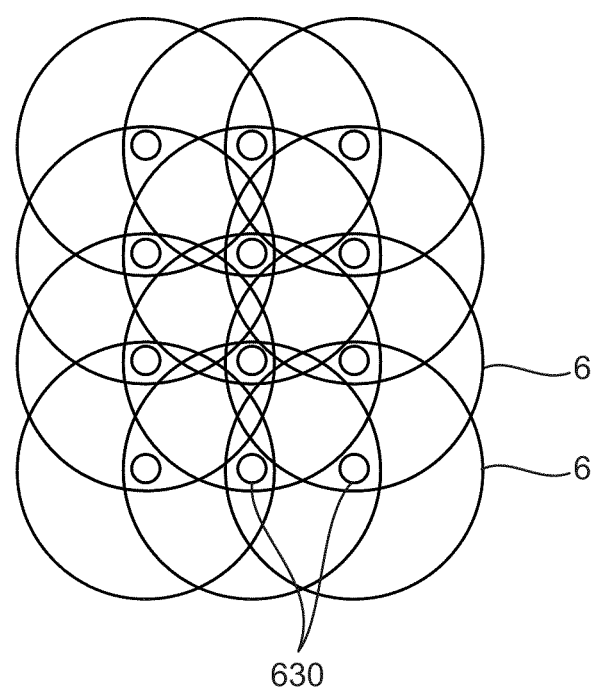
FIG. 15 is a representation of an ultrasound treatment pattern in accordance with an embodiment.

Using the varied sizes along with multiple treatments for a single location allows a number of variations. For example, as shown in FIG. 15, large halo fields may be overlapped so that each location has four halo effects at each lesion field. The system may be arranged so that the cumulative power applied at each lesion field may be sufficient to cause cellular necrosis and collagen fibril denaturing.

Figure 4A:
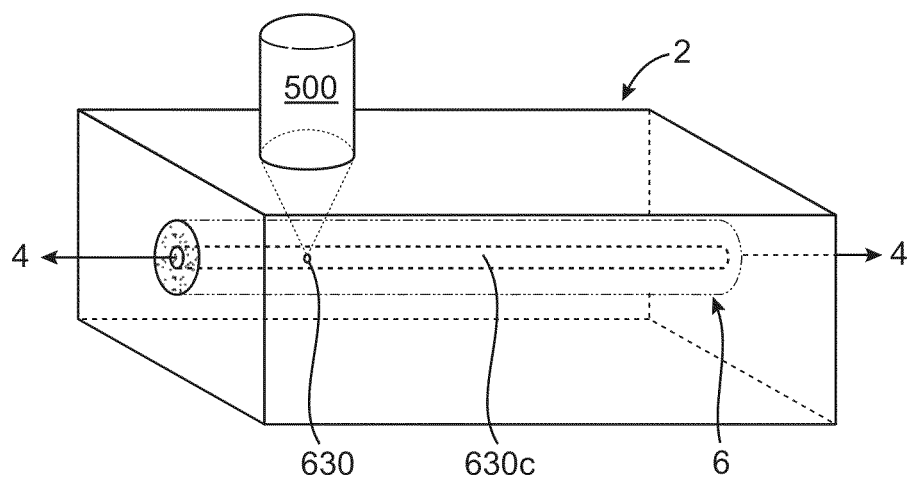
Figure 4B:
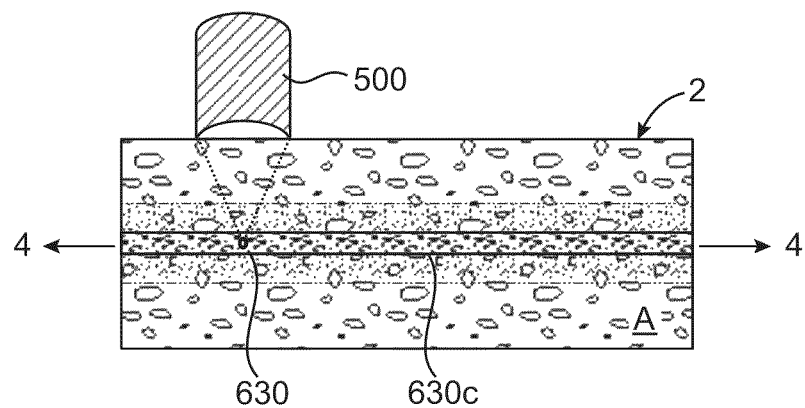
Figure 4C:
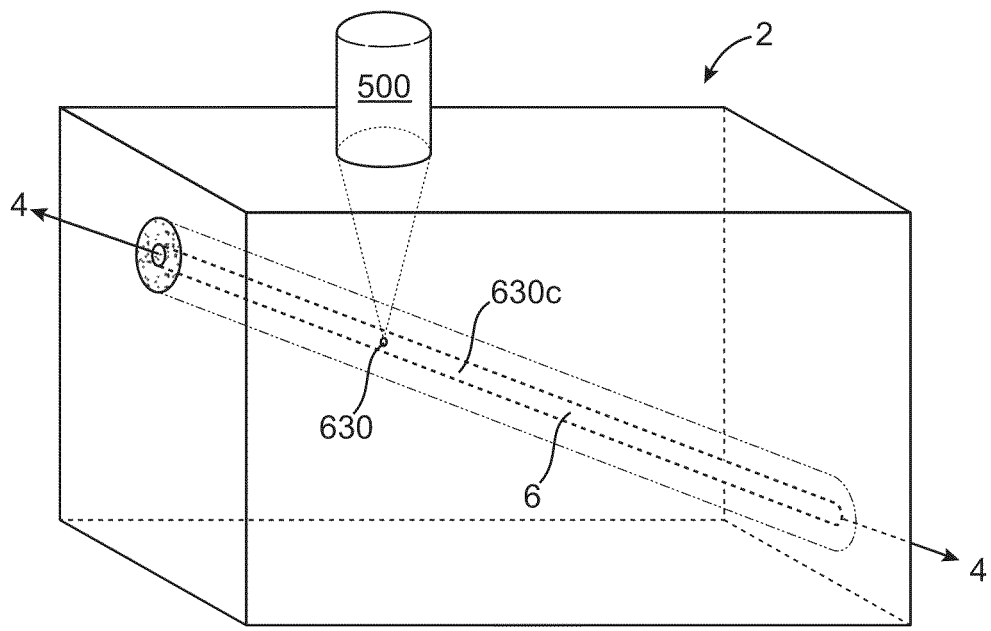

The motion of the transducer over the patient skin can follow any number of patterns. In one aspect of the systems and methods of the invention, a basic motion is shown in FIG. 4A. Here a transducer 500 may be moved in a linear path over the patient skin. The transducer has a focal zone 630 which creates a lesion field. The transducer may be moved in a controlled manner so the lesion field formed by the HIFU therapy transducer may form a single, contiguous line of destroyed tissue 630c. The axis of the focal zone in tissue is referred to herein as the scan line 4. Surrounding the scan line 4 can be a region of thermal effect raising the local tissue to temperatures sufficient to kill adipose tissue and denature collagen fibrils. This halo field 6 about the scan line 4 represents the volume of tissue which receives sufficient thermal radiation from the lesion field 630, 630c to also be destroyed and denatured. The halo 6 may be large or small depending on how quickly the transducer is moved, and how much power the transducer produces. Here a single scan line 4 is shown within a single treatment site 2 for clarity. A cross section view of a scan line 4 is shown in FIG. 4B. FIG. 4C illustrates a scan line having a varying depth component.

For multiple treatments at the same location, a scan line may be repeated. Alternatively, scan lines may cross or overlap to provide a desired accumulation.

Figure 3A:
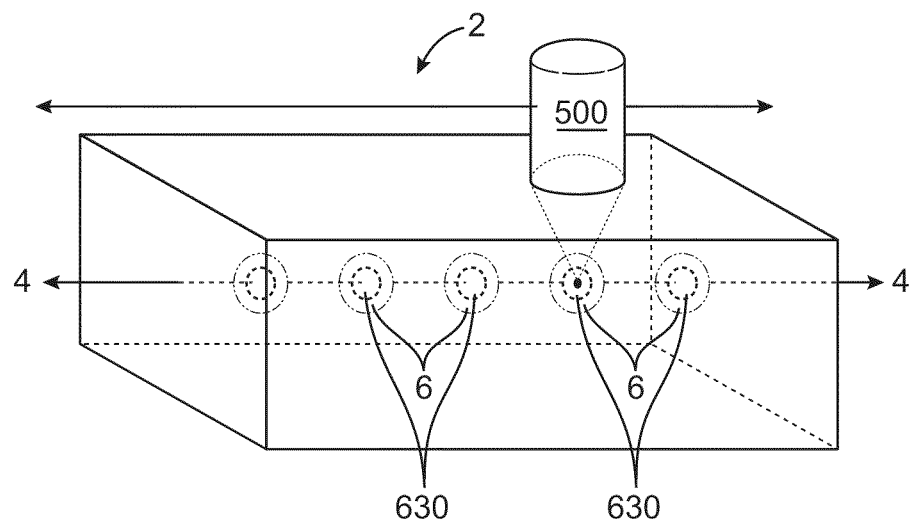
FIGS. 3A-3D, 4A-4C, 5A-5D illustrate various treatment approaches.
Figure 3B:
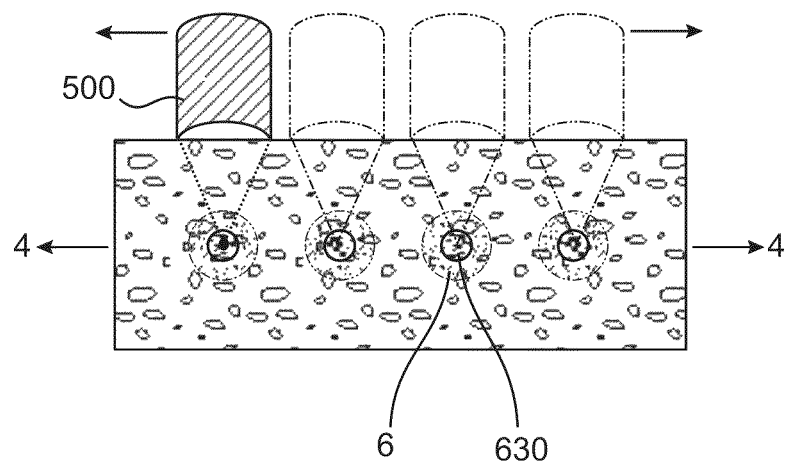
Figure 3C:
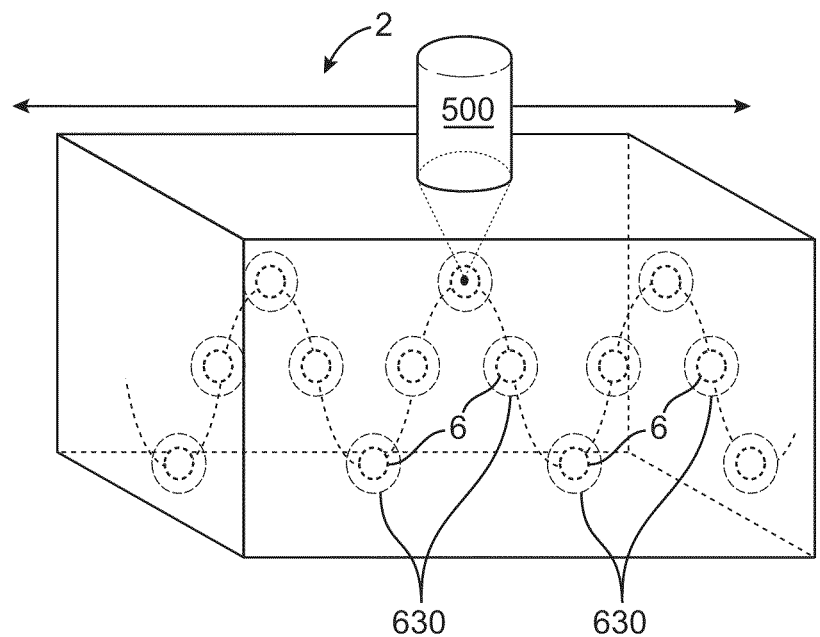
Figure 3D:
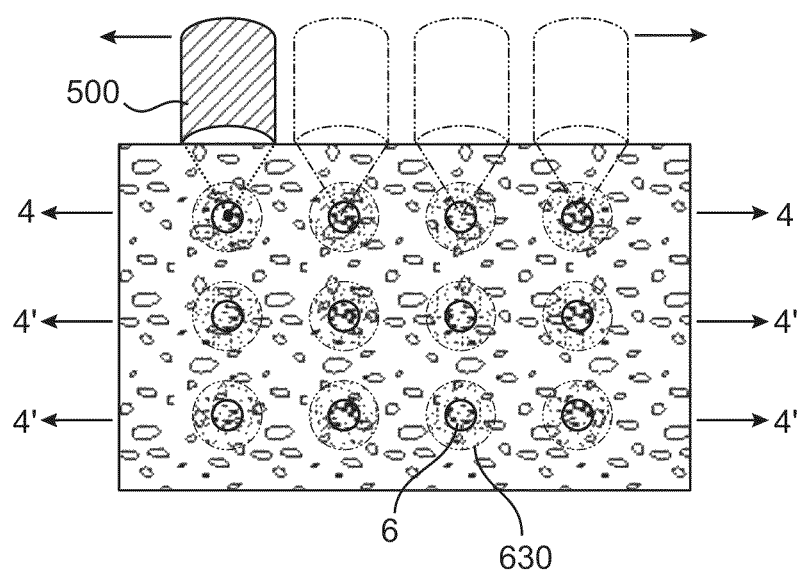

In another embodiment, the transducer 500 may be made to produce high intensity pulses or pulse bursts (rapid sequence of discrete pulses) to produce discrete lesions 630 along a scan line 4 (FIG. 3A). In this embodiment, the transducer may be moved over the patient skin surface and the transducer programmed to deliver discrete bursts of HIFU ultrasound energy to produce individual or discrete "cells" of destroyed tissue. The burst of ultrasound energy can produce any variety and number of discrete lesions in the tissue. A halo 6 may also be found surrounding each lesion depending on the operating parameters of the transducer. Again, the pattern of lesion fields and halos are also presented in cross section shown in FIG. 3B. FIG. 3C provides a view of a series of discrete lesions formed in tissue where the lesions are produced sequentially at varying positions along the X, Y and Z axis. FIG. 3D illustrates a series of discrete lesions where the lesions are produced in vertical stacks. The halo 6 of each lesion field may overlap (not shown) if desired.

Figure 5A:
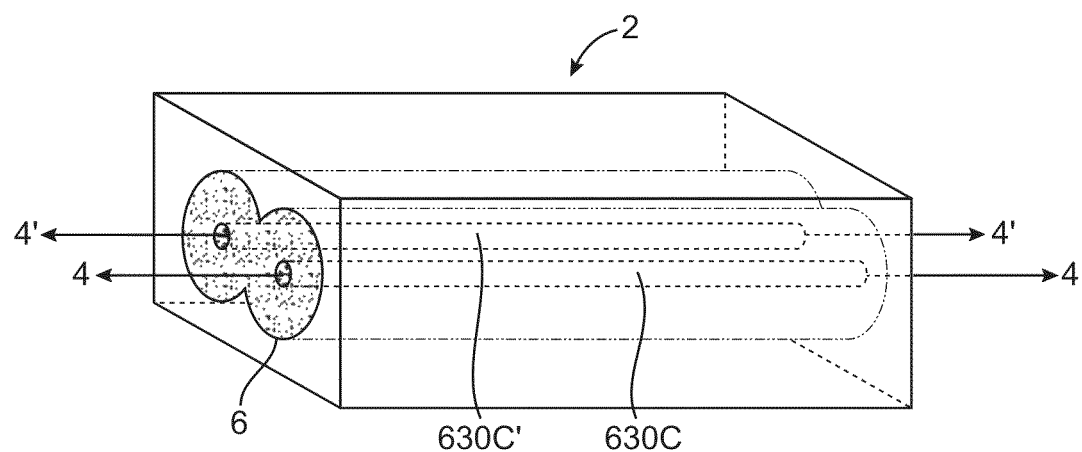
Figure 5B:
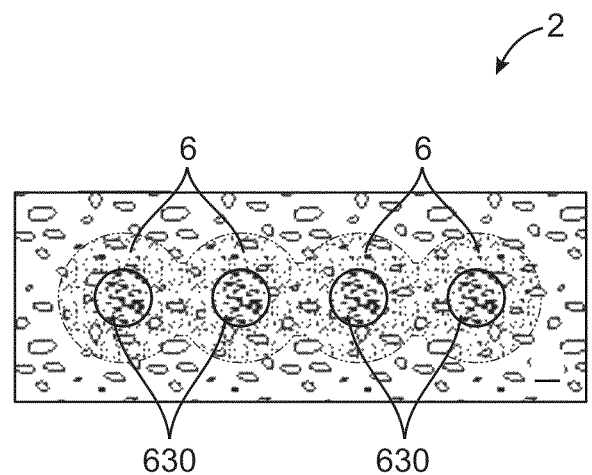
Figure 5C:
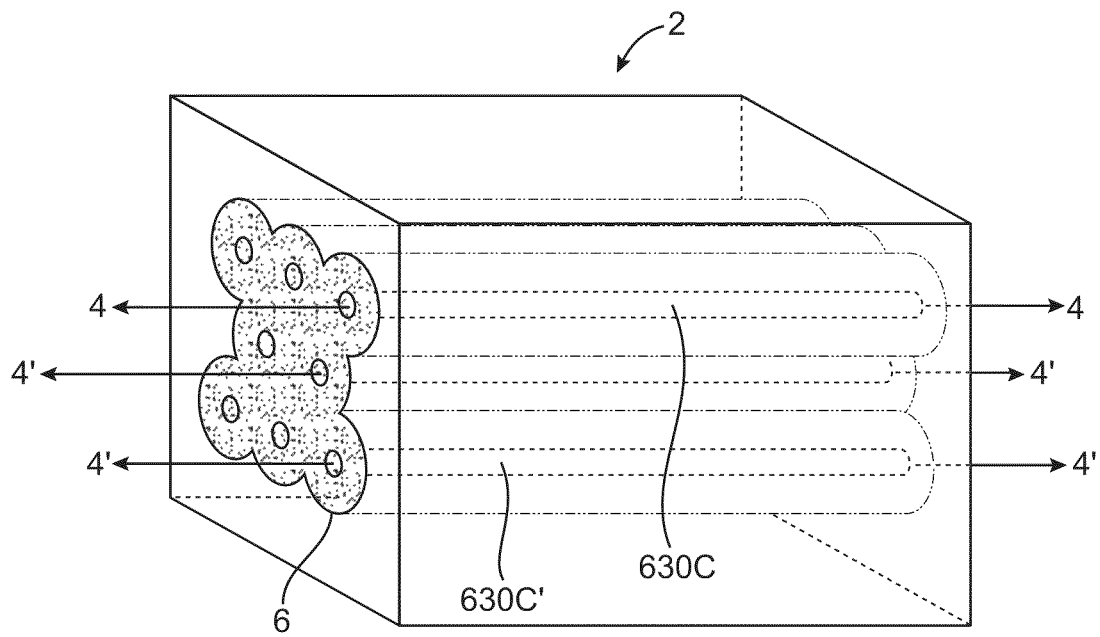
Figure 5D:
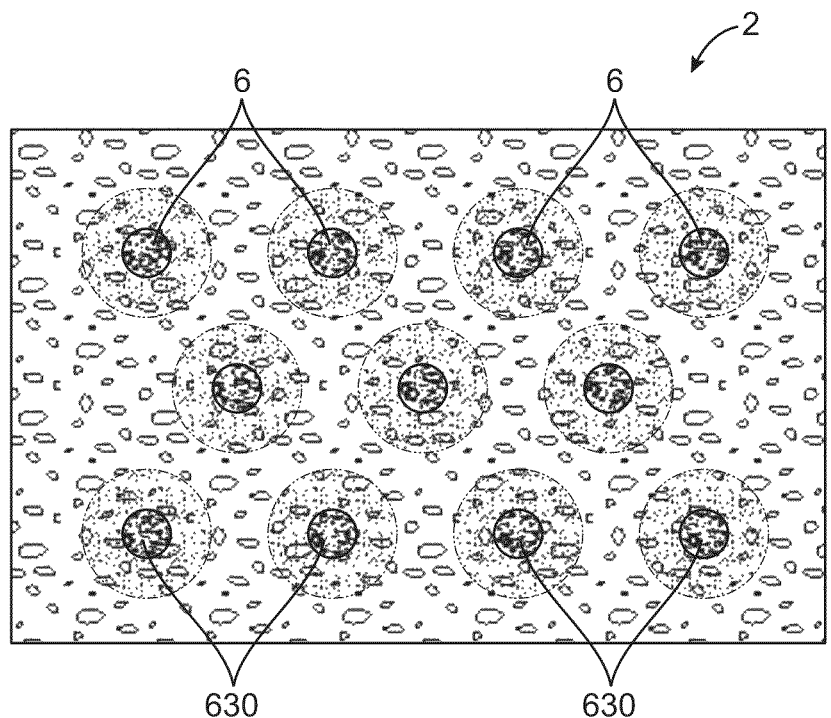

Another embodiment for applying ultrasound energy is illustrated in FIGS. 5A-B. Here two scan lines 4, 4' are shown in close proximity so that the contiguous lesion fields 630c, 630c' are parallel. The halo zone 6 of each scan line run together to form a region of cooperative effect and enlarge the halo zone. Multiple scan lines may be placed side by side to form a large layer of mechanical and thermal effect (FIG. 5B). FIG. 5C provides a series of scan lines $630c$, $630c_{x-n}$ arranged in a three dimensional stack, one with overlapping halo regions 6 (FIG. 5C), and one without overlapping halo regions 6 (FIG. 5D)

For multiple treatments at the same location, individual scan lines may be repeated at the same location, or slightly moved over so as to overlap a previous line. Alternatively or in addition to this arrangement, scan lines may cross or overlap to provide a desired accumulation. A large number of scan lines may be utilized for a treatment area with several overlaps in the scan lines and so that cumulative power at most or all locations is sufficient for cellular necrosis and collagen fibril denaturing. Collagen denaturing can occur at temperatures above 37° C. However denatured collagen at temperatures close to normal body temperature may recover, relax and resume their normal length. In an aspect of the present methods, collagen in the treatment zone may be exposed to temperatures above 37° C. In another aspect, collagen fibrils in the treatment zone can be exposed to temperatures above 46° C. and in another aspect, the temperature may be about 56° C. or greater. The higher the temperature the collagen fibrils are exposed to, the shorter the length of time needed to achieve the desired effect. When the exposure is at 46° C. the collagen fibrils need to be incubated at that temperature for at least several minutes, however exposure of collagen fibrils to temperatures near or above 56° C. may be done in less than a few seconds. "Collagen Fibril" refers to the collagen material found in adipose tissue or sub dermal regions where collagen concentration tends to be sparse and used by the body as a lattice connective tissue rather than a major structural component (contrast with regions like the nose, ears, skin or tendons and the like). Contraction of collagen fibrils refers to using thermal energy to denature the collagen and force the collagen fibrils to shorten lengthwise.

In an aspect of the methods of the invention, adipose tissue may be heated using HIFU energy so the temperature in the lesion field is raised as high as practical and as fast as possible. Parameters of the HIFU transducer may be adjusted to produce the desired fast heating needed to destroy adipose tissue and denature collagen fibrils. The fast heating can be balanced with the volume and dimensions of the adipose tissue to be treated. The longer the transducer remains active on one location, the larger the halo field. The moving of the HIFU transducer and the applying of therapeutic ultrasound energy should not be used to produce lesion or halo fields which extend beyond the dimensions of the intended tissue volume.

Although using higher power and pressure produce faster results, using higher power may cause a patient some pain. The same or a similar effect may occur, however, by using multiple lower power treatments at a same location so that there may be an accumulation of power resulting in a similar treatment.

Additional parameters that affect the size of the lesion and halo fields are those parameters electronically controlled through the transducer, and parameters of the transducer itself. These parameters include (but are not limited to) power, frequency, duty cycle, focus, size (of transducer), and pulse repetition frequency.

Figure 6:
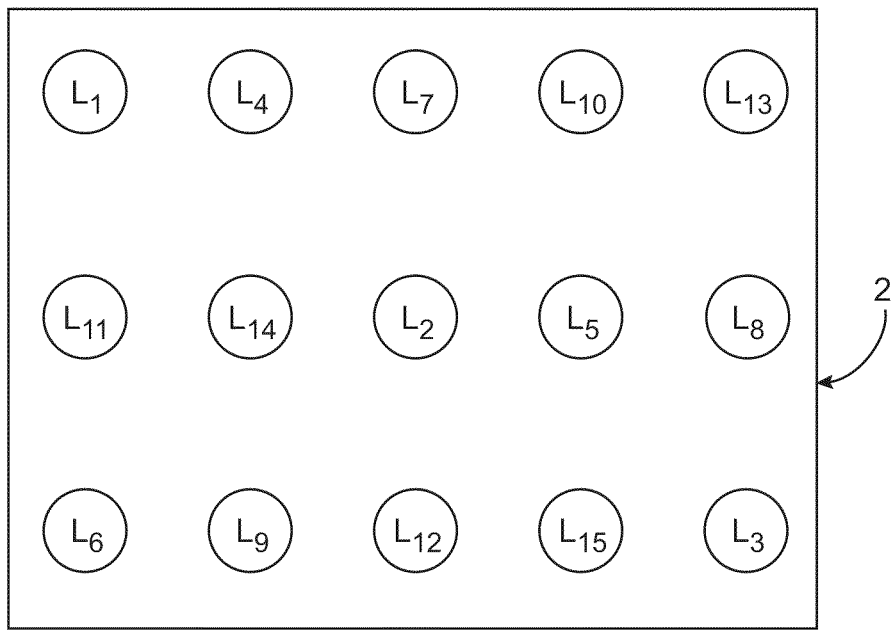
FIGS. 6-8 illustrate various ultrasound treatment patterns.

In some applications, the size of the lesion and halo fields may be minimized. This may be required where the adipose tissue depth necessitates a tightly controlled lesion and halo field due to proximity of muscle, bone, organs or skin. This can be accomplished by distributing the individual lesion fields within a treatment site apart from each other in both distance and time. If the treatment site is represented by a defined field area 2, then the individual spot lesions may be laid down one at a time in a sequence from $L_1$ to $L_{15}$ (FIG. 6). For multiple treatments at each location, the sequence may be repeated or may be performed in a different order. Here the lesions are temporally separated as well as being spatially separated. This pattern allows for the individual lesions to have a minimum cooperative thermal effect between lesions. The size of each lesion ($L_{1-n}$) may also be controlled by adjusting the parameters of the ultrasound transducer used in the treatment.

Figure 7:
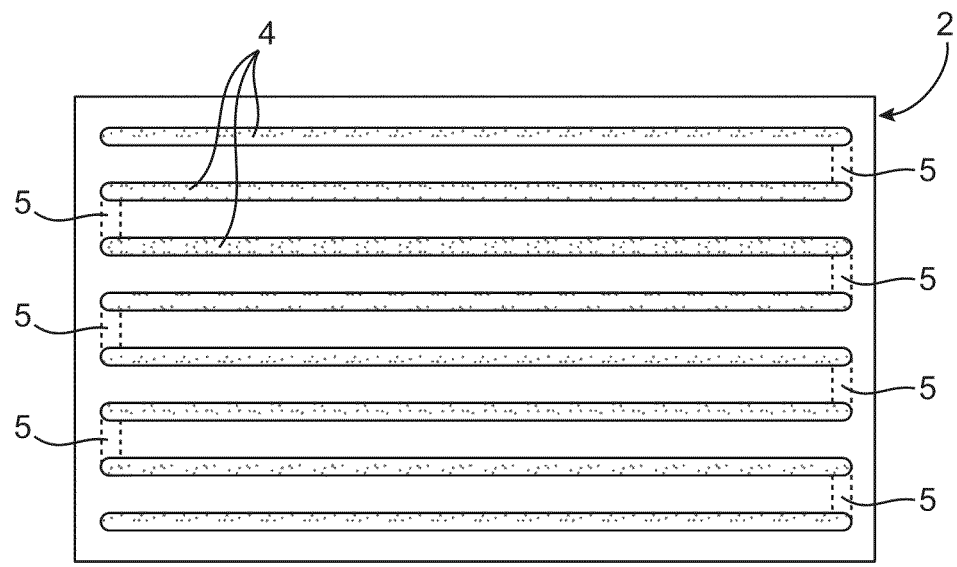

Alternatively, the lesion and halo fields may be maximized by permitting the HIFU transducer to produce contiguous lesion fields and cooperative halo fields. An example of such a maximizing movement scheme is illustrated in FIG. 7. In an embodiment, the energy required to produce cellular necrosis and collagen contraction may be lessened due to the co-operative effect of having the transducer operate in narrowly spaced treatment lines and in rapid succession of laying down treatment lines near each other in both time and space. Movement of the transducer can be machine controlled for uniformity and simultaneous control of the transducer. The transducer can treat patient tissue volume by moving over the surface of the tissue volume in any variety of patterns including, but not limited to, spiral, raster scan, or any other pattern. Thermal cooperation can be maximized by delivering the ultrasound energy as a contiguous lesion field 630 within the treatment site 2. A raster scan type pattern (FIG. 7) may be used with a relatively close line spacing to provide for a maximum of thermal cooperation to produce a large halo region. The horizontal scan lines 4 may be connected with vertical transit lines 5 where the transducer is active, or the vertical transit lines may be "empty" if the transducer is not active while moving vertically. Likewise the spacing between the horizontal lines 4 may be close together or physically overlapping to provide for the maximum overlap of ultrasound energy. For multiple treatments on a same location, as described above, the raster pattern may be repeated or different crossing or overlapping patterns may be used to provided desired accumulation at each location. Careful planning and consideration in the applying of ultrasound energy in the methods described herein can produce the desired volume of tissue modification in both the amount of adipose tissue destroyed, and collagen denatured.

A balancing of speed (velocity of the focal zone in the tissue being treated) and the power and intensity of the transducer may be used to produce the desired effect. A method of determining the various parameters to use in a tissue modification is now described. In an embodiment, there is a method of reducing adipose tissue volume in a patient using high intensity focused ultrasound. The method comprises the steps of determining a volume of adipose tissue to be treated; marking out a corresponding surface area of skin and applying high intensity focused ultrasound energy to said area in a manner sufficient to induce the gradual destruction of said adipose tissue and denaturing of collagen fibrils, the energy flux being of at least 35 J/cm². Operationally the speed of destruction may be quickened by providing higher EF values. By scanning the transducer over a volume of adipose tissue at higher EF values, the amount of time needed to achieve adipose tissue necrosis and collagen fibril denaturing can be reduced. Using EF values between 90 and 225 Joules per square centimeter allow for the desired treatment to be done quickly. Further increasing the EF to higher values also produces viable results under certain conditions, going as high as 460 J/cm².

Accumulation can provide a desired EF value without the application of high energy flux pulses. For example, two separate treatments, each having 33 J/cm², may result in an accumulated EF of 66 J/cm², without having to resort to a treatment exceeding 35 J/cm². As such, efficacy may be enhanced with greater patient tolerance.

By using a predetermined energy flux value, the transducer can be programmed to consistently and accurately deposit the same amount of energy into each of the lesion fields (also referred to as the focal zone). Through experimentation and analysis, we have found that tissue ablation of adipose tissue and collagen contraction can occur at energy fluxes above 35 joules per square centimeter. Variations in desired outcomes and tissue variations from patient to patient make calling out an exact energy flux figure impossible. However empirical data from multiple study sources suggest the energy flux value, from cumulative or a single treatment, should be greater than 35 joules per square centimeter and are probably most efficacious for the dual purpose of destroying adipose tissue and denaturing collagen fibrils at or above 109 joules per square centimeter.

In a physical embodiment of the present invention, there may be an apparatus for the delivery of therapeutic ultrasound energy into a patient. The apparatus having at least one ultrasound transducer adapted for being moved while applying therapy and being capable of depositing an energy flux (EF) greater than 35 J/cm² as measuring the energy crossing into the body at the skin line, wherein EF is determined by the formula:

$$[(p)\times(l/v)\times(dc)\times(nl)]/(sa)$$

wherein
p=power,
l=line length,
v=velocity,
dc=duty cycle,
nl=number of lines
and
sa=scanned area.

The formulation provided provides for a calculation when the transducer is moving continuously while applying ultrasound energy. Alternatively for a treatment program where the transducer is not moving between therapy applications, the EF can be calculated using the following modified EF equation.

$$EF=[(p)\times(t)\times(dc)\times(ns)]/(sa)$$

wherein
p=power,
t=on-time per lesion,
dc=duty cycle,
ns=number of lesions,
and
sa=scanned area.

Variations in the formula can be derived by those skilled in the art to determine the proper calculations for a therapy program having a mixed set of moving and non-moving treatment sites. The therapy controller may allow for wide variation in parameters which a user may manually feed into the therapy controller prior to each application of ultrasound. The therapy controller determines which variables are to be used and weights them accordingly. An example of a medical instrument system for use with the methods described herein is further described in co-pending U.S.

patent application Ser. No. 11/027,912 entitled "Ultrasound Therapy Head with Movement Control" the contents of which are herein incorporated by reference.

Another example is described in co-pending U.S. patent application Ser. No. 11/026,519 entitled "Systems and Methods for the Destruction of Adipose Tissue" filed on Dec. 29, 2004, the contents of which are herein incorporated by reference. The apparatus for the delivery of therapeutic ultrasound energy into a patient has a scan head, suspension device for supporting the scan head, and a therapy controller. The therapy controller is adapted to monitor the position and energy deliver of the scan head. This apparatus may be used to deliver multiple treatments to the same location by having the scan head return multiple times.

Figure 16:
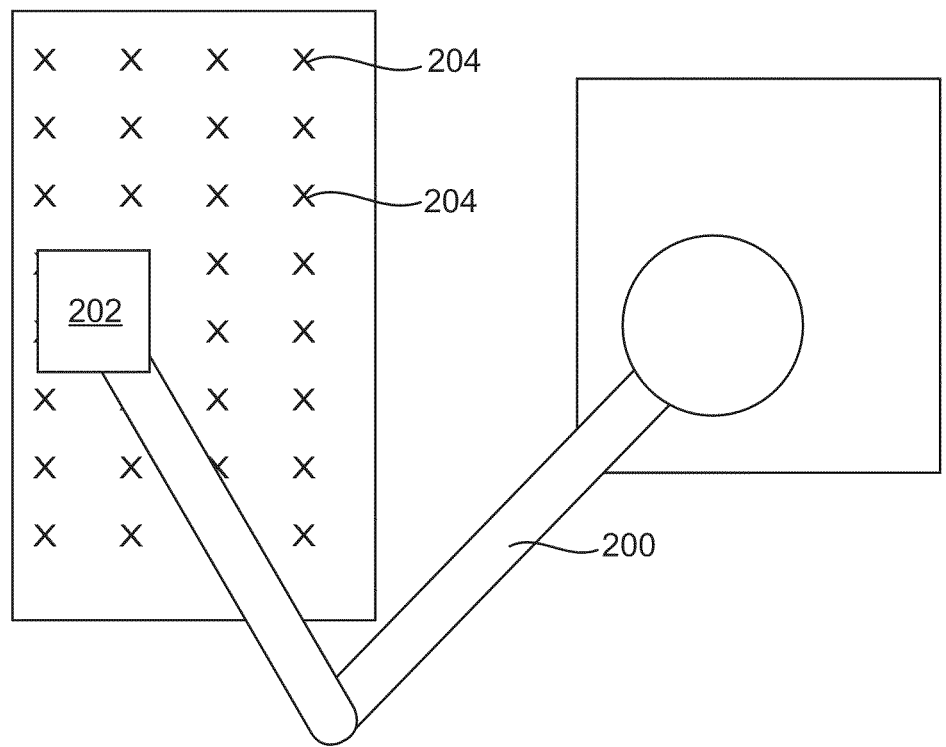
FIG. 16 a block representation of a robot arm apparatus that may be used in a procedure in accordance with an embodiment.

Another example is shown in FIG. 16, where a robot arm 200 moves a scan head 202 over multiple markers, for example on a patient's body. The scanner head 202 may be directed by a physician to the markers, and then instructed to apply a treatment. The robot arm may remember the position, for example using kinematic information, and after the physician has placed the scanner head at each treatment location, return automatically to each of the locations so that multiple treatments may be applied to the each location.

Alternatively, the robot may remember a location, for example via kinematics, and count the number of applications applied by a physician. As still another alternative, the scanner head may include optical recognition hardware, and may automatically find a marker and apply a treatment.

The various parameters of the Energy Flux equation can be programmed into the therapy controller. The apparatus may have some parameter data programmed in fixed memory and not adjustable by the user. Some elements may include maximum and minimum settings of the transducer to prevent the apparatus from being operated in an unsafe manner.

A user can provide variables into the system to help the system determine the proper EF to be used during a procedure. For example if the user wishes to increase cooperative heating between scan lines, the scan lines (nl) may be set to a higher value. Alternatively the velocity may be reduced to promote larger halo fields, or the velocity may be increased to decrease halo fields as might be required for regions of adipose tissue which have smaller margins.

Figure 9:
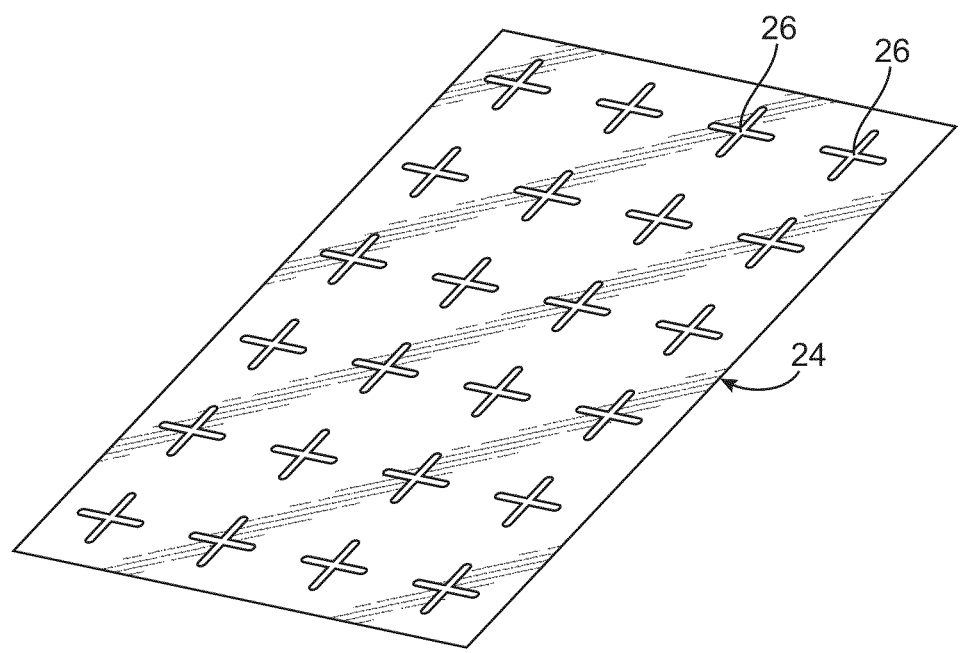
FIG. 9 illustrates a stencil.

A stencil or template 24 can be used to assist a physician in planning the treatment (FIG. 9). The template 24 has a series of apertures 26 in the form of "crosshairs" which can be used to guide the ultrasound transducer during the treatment procedure. The template 24 may be created so the apertures match the foot print of the transducer to be used (or therapy device depending on the ultrasound system selected). The template may be used across the skin prior to the creation of contour lines or prior even to the evaluation of the adipose tissue in the target region. A physician may mark the contour lines and crosshair marks after making the determination of suitable adipose tissue depth in the patients target treatment region.

Figure 2:
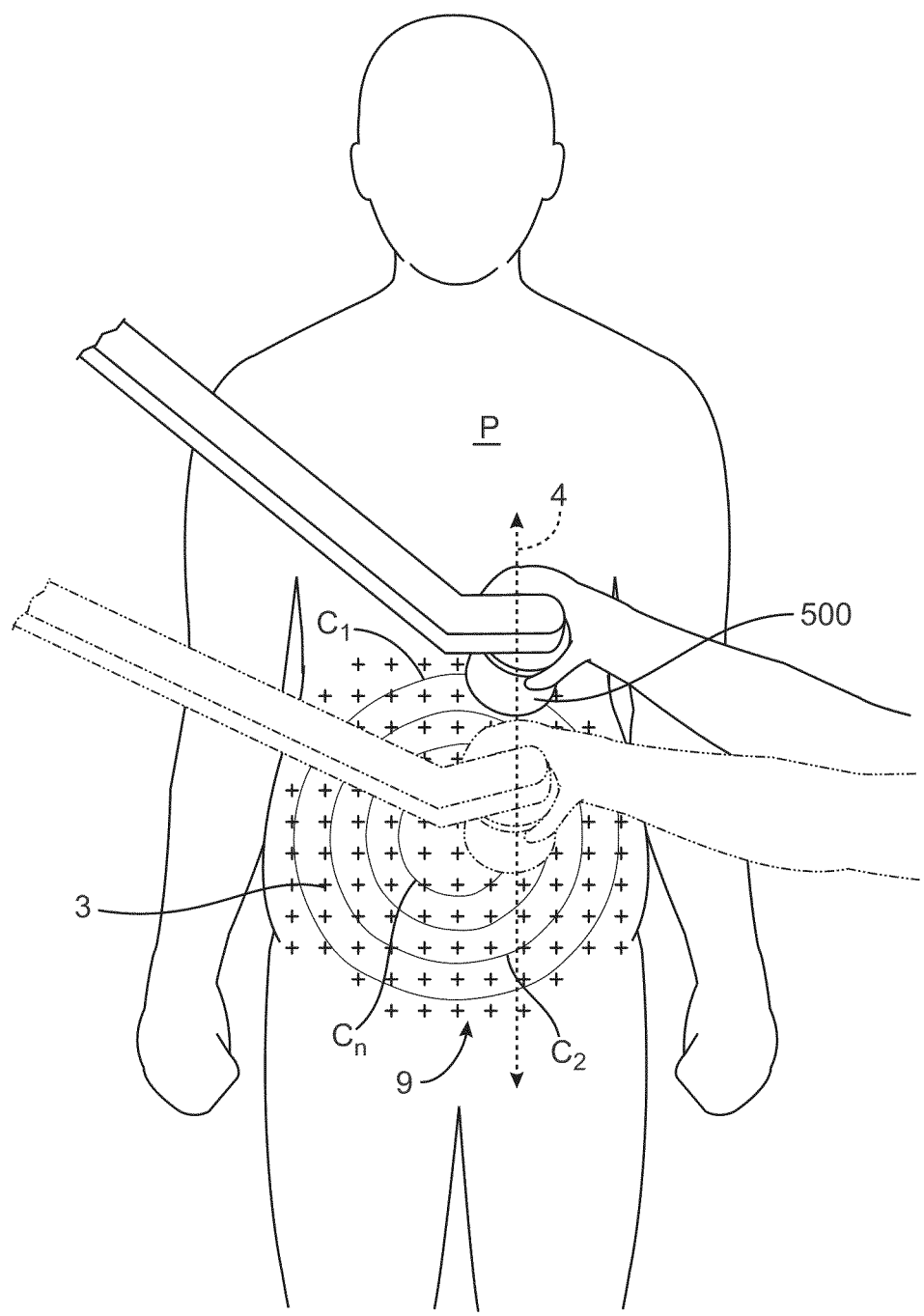
FIG. 2 illustrates the motion of a HIFU treatment device over the patient.
Figure 10:
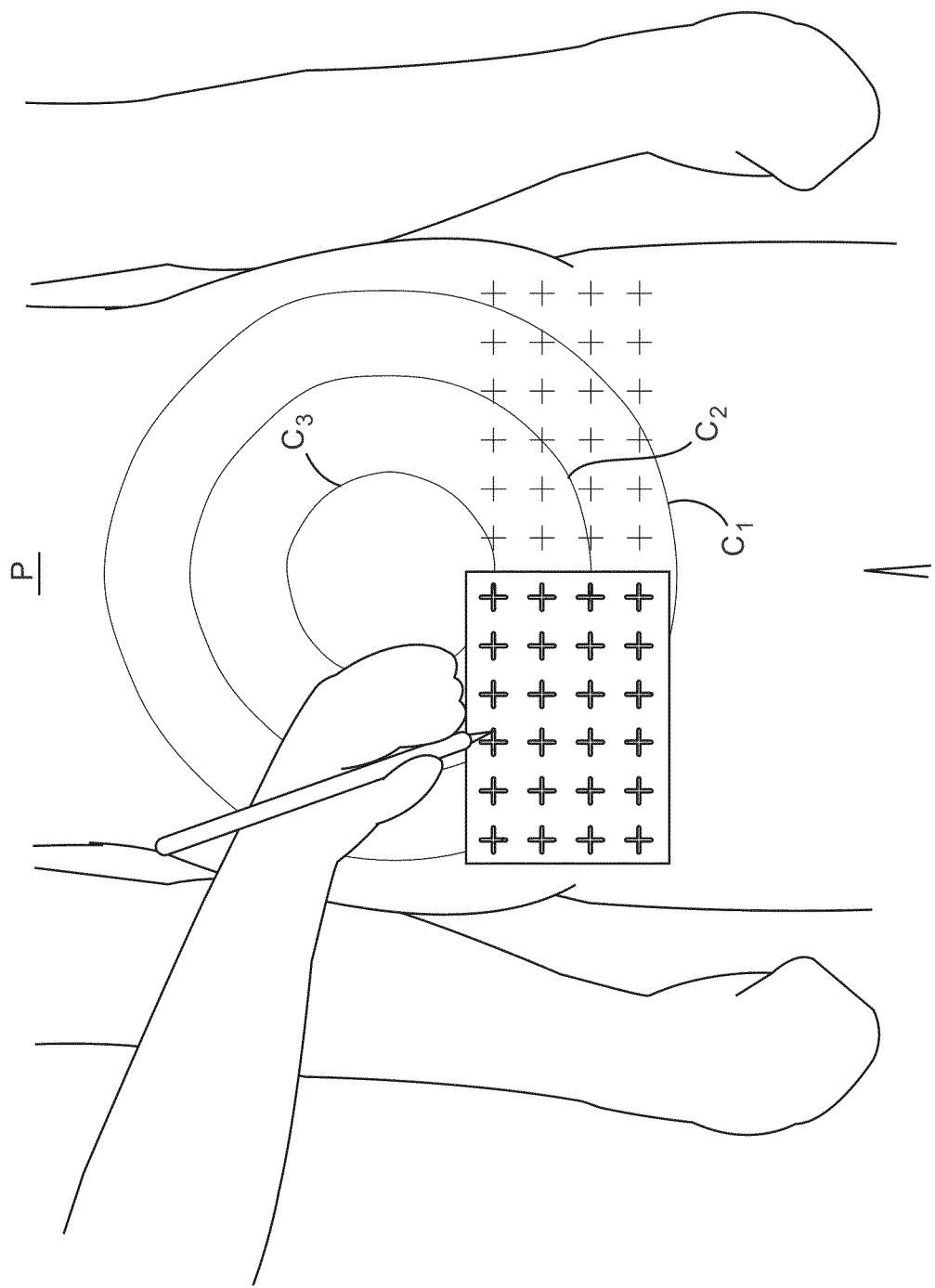
FIG. 10 illustrates the use of a stencil on a patient.

The stencil 24 can be laid across the patient (FIG. 10) and then the crosshairs drawn in using a medical marker. The combination of crosshairs and contour lines shown in FIG. 1 combine to provide visual markers for the safe placement of a HIFU transducer in an ordered fashion (using the guide marks) within a known depth of adipose tissue (using the contour lines). Once the two markings are on the patient, the physician need only line up the ultrasound treatment device with the crosshairs and contour lines (FIG. 2) to produce a mosaic of treatment sites 2 (FIG. 11).

The volume of tissue to be treated can be done using techniques already adopted by physicians in the ordinary practice of procedures like UAL. The physician can use a manual pinch test, calipers or diagnostic ultrasound to determine the depth of the fat tissue to be treated and draw circles around the region to be treated, similar to relief lines on a topographical map. The individual marks from the stencil may be made before or after the volume is determined. The contour lines representing varying levels of tissue volume, and therapy head land marks overlap to provide the user with a defined safe area to treat, as well as a guide for treatment using the ultrasound therapy head.

Figure 13:
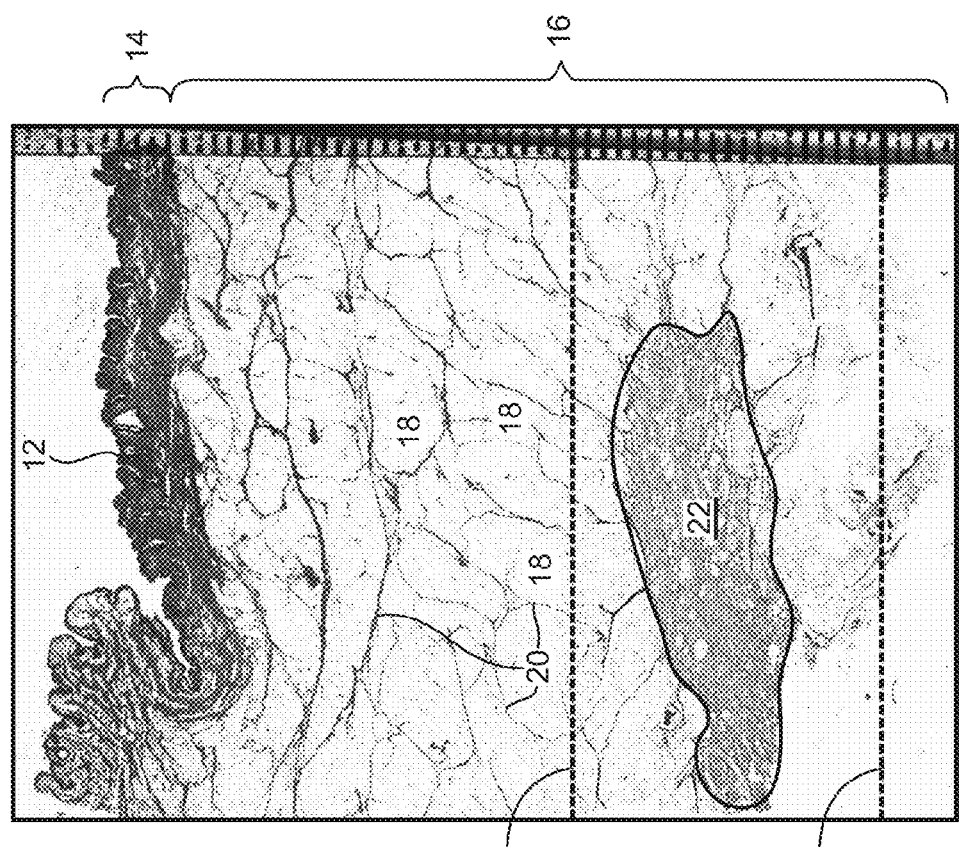
FIGS. 12-13 show histology slides of actual treated tissue.
Figure 12:
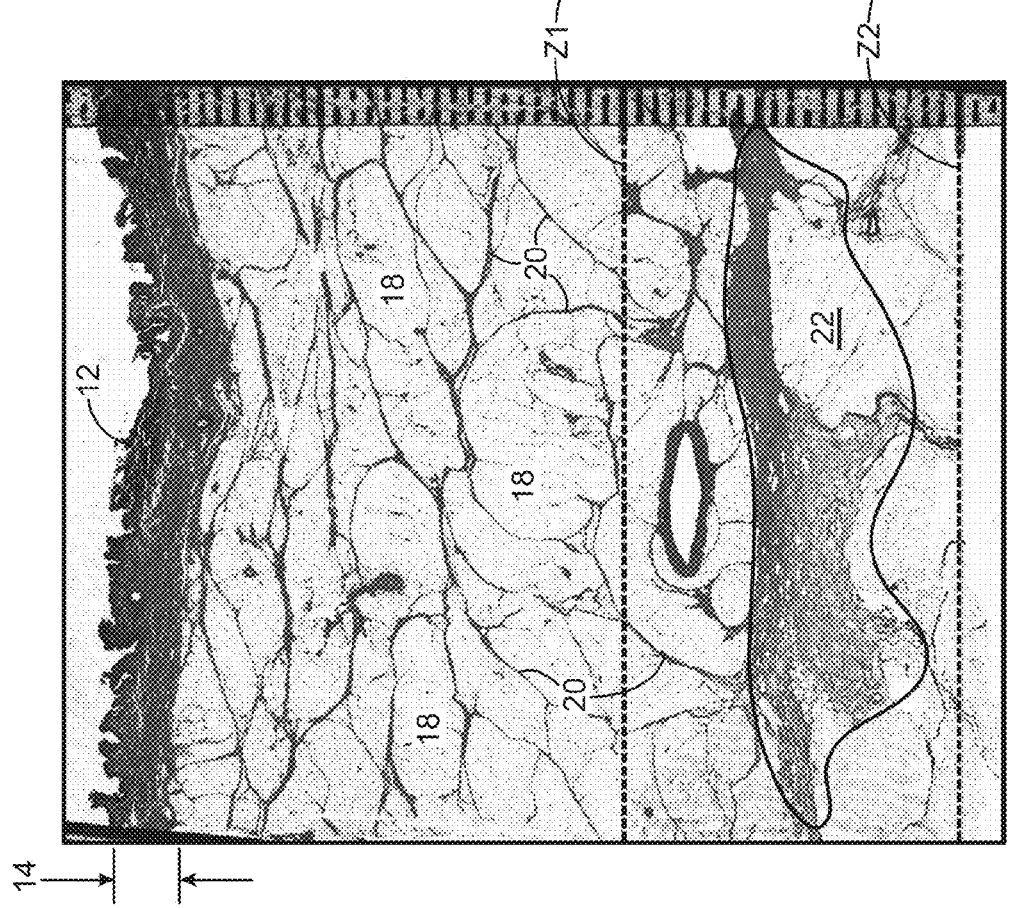

Proper utilization of the methods described herein can reduce the volume of a region of adipose tissue. Histology slides of tissue using the methods described herein are shown in FIGS. 12 and 13. These histology pictures show both the skin line 12 and skin layer 14 are undamaged. There is also shown a region of adipose tissue 16 having a relatively safe depth for this type of treatment. The treatment zone is found between the markers Z1 and Z2. Normal adipocytes (fat cells) 18 and normal collagen fibrils 20 are shown between the skin layer 14 and the treatment zone Z1. Within the treatment lines Z1, Z2 are shown two regions of heavy collagen population and nearly complete lack of adipocyte structures. The lesion field 22 shows both the collapse and destruction of adipose tissue and the denaturing of collagen fibrils which contract the tissue volume as the destroyed tissue mass is gradually removed from the body (through the body's natural wound healing response). The reduction of adipose tissue volume in this manner provides a similar long term result to liposuction. Since the tissue loss is gradual, there is no sudden looseness of the skin layer, nor skin deformation observed immediately after a patient undergoes a treatment using the methods described herein. The tissue volume reduction varies from patient to patient.

The results illustrated may be achieved by using the system and methods described herein in a single pass (treating a volume of adipose tissue once) or multi-pass (treating a volume of adipose tissue more than once). The single pass may be a series of horizontal lines (made substantially parallel to the skin surface during a single pass treatment) so the treatment area forms a roughly X-Y plane. A single pass averages about −2.0 cm in waist circumference. In a multi pass treatment plan more than one X-Y plane can be made at the same or different tissue depths as measured from the skin line. The necrosis of adipose tissue resolved over a course of 8-12 weeks from three dimensional treatment (using a series of two dimensional treatments in sequence to produce a three dimensional over all treatment) produced observed changes in waist circumference recorded between +4 cm to −9 cm using a variety of treatment profiles described herein, with an average reduction of 4.6 cm. This early data suggests the effectiveness of a three dimensional type of treatment in humans produces an unanticipated result and far exceeds projected results based on using multiple layers using only an X-Y plane from animal studies (which showed no difference from a single pass treatment).

In an implementation of the various three-dimensional treatment embodiments, the medical ultrasound therapy system may have a therapy head including at least one high intensity focused ultrasound transducer and a controller. The controller may have a data store storing information about a three dimensional treatment profile for the therapy head and a processor coupled to the data store. The processor generates a three dimensional treatment cycle for the therapy head in accordance with the information. The three dimensional treatment cycle includes treatments by the therapy head at a plurality of different depths.

The data store may store data in volatile or nonvolatile form. The data may be stored on various computer readable media, including a hard disk, EPROM, a removable magnetic disk, a removable optical disk, magnetic cassettes, flash memory cards, digital video disks, Bernoulli cartridges, random access memories (RAMs), read only memories (ROM), and the like, as non-limiting examples.

Figure 17:
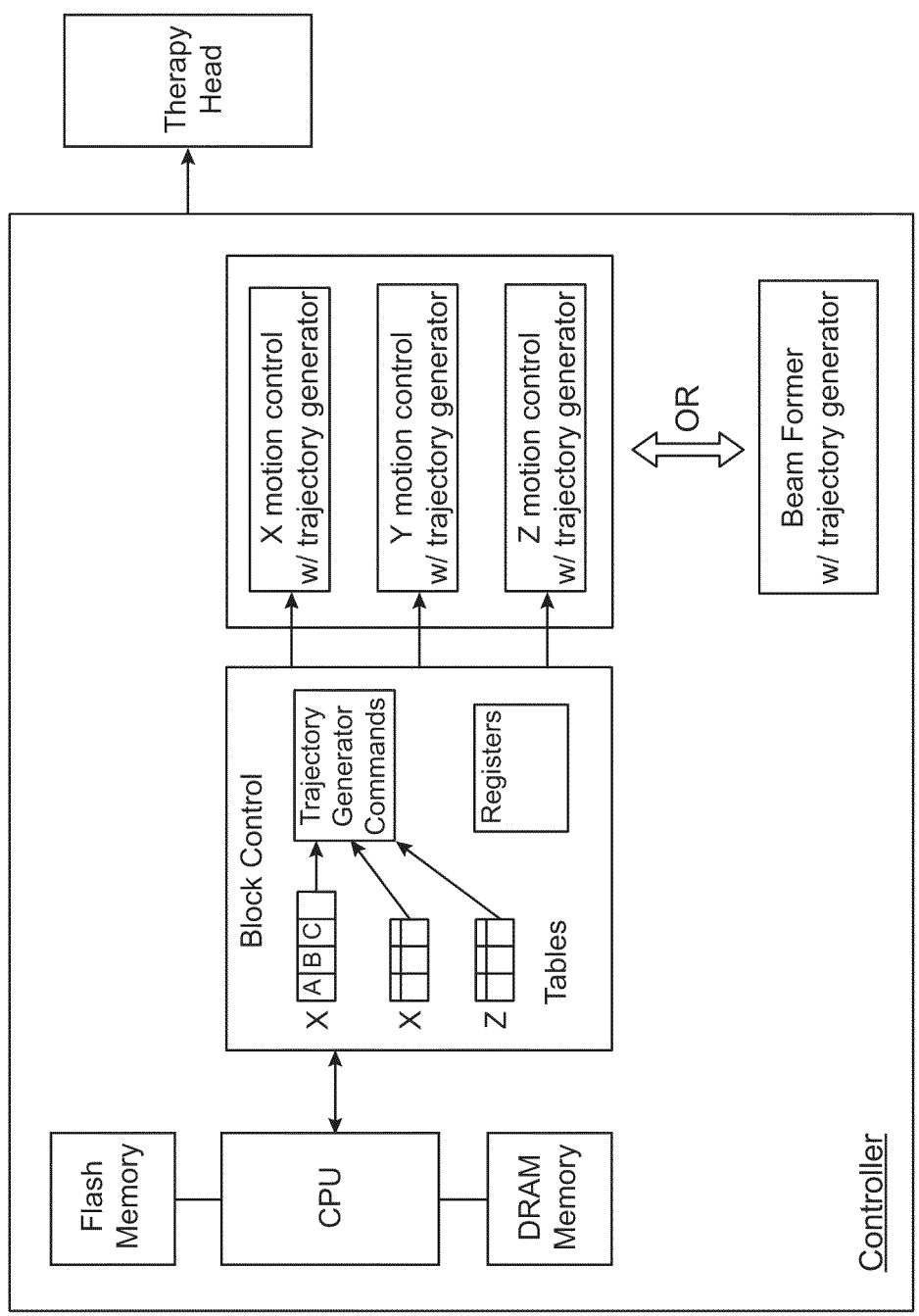
FIG. 17 provides a block diagram of system components used for the three dimensional control of a therapy head.

Schematically the components of an embodiment are shown in FIG. 17. The therapy head contains an ultrasound transducer. The therapy head may be connected to a controller. The controller may be a standard control (i.e., a device or mechanism used to regulate or guide the operation of a machine, apparatus, or system), a microcomputer, or any other device that can execute computer-executable instructions, such as program modules. Generally, program modules include routines, programs, objects, components, data structures and the like that perform particular tasks or implement particular abstract data types. A programmer of ordinary skill in the art can program or configure the controller to perform the functions described herein.

In an embodiment, the controller includes a CPU, persistent and DRAM memory types, a block control, and one or more motion control elements. The data store storing information about a three dimensional treatment profile for the therapy head is kept, in accordance with an embodiment, in flash memory. The flash memory provides persistent memory to the system when the power is off. On start up, the data store is loaded into DRAM for access by the block control. In preparation for the medical procedure, a user selects one or more parameters about the tissue region to be treated. The input from the user is provided to the CPU through an input device such as a GUI, keyboard or mouse controller. Once the parameters are selected by the user, the system accesses the DRAM for the appropriate X axis, Y axis and Z axis commands for controlling the motion of the therapy head. The data store provides appropriate data so trajectory generators are provided to the X, Y and Z motion controllers, each having their own trajectory generator. In an embodiment, this data may be provided in the form of tables, although other data formats and/or schemas may be used.

The controller may also provide movement control to the robot arm 200 if a robotic arm is used in conjunction with the therapy head.

Alternatively, the therapy head may be held stationary, and the various X, Y and Z axis motion control operations may be taken over by an electrically steered transducer. An annular array could provide Z axis control, allowing the therapy head to be driven by a beam former with Z axis trajectory control, along with the X and Y axis motion control and respective trajectory generators. Another option is to have a 2D array where allowing the beam former to take over any two axes from the motion controller, or a 3D array allowing a beam former to provide three dimensional electronic control of the position of the focal region produced by the transducer in the therapy head.

Still another embodiment may use a the controller to provide instructions to a technician to position, move, operate, and/or otherwise control the therapy head and/or transducer to perform treatment in accordance with information in the data store. This information may be provided on a display, for example, in sequential steps, or as a print out or in another form.

The block control may be executed using a Field Programmable Gate Array (FPGA), Application Specific Integrated Circuit (ASIC), or general purpose computer CPU. In some instances where a general purpose central processing chip is used, the data store may also require one or more specific software application(s) to help interpret the library tables of the data store and execute the control of the therapy head as desired. Similarly, as described above, different memory storage may be used for the data, such as the flash memory may be any persistent memory device, and the DRAM may be any volatile memory device accessible by the control block or CPU, including an integrated memory module on the hardware component of the control block.

Additional components may be incorporated to the controller depending on the motor assembly used to move the transducer inside the therapy head (e.g. conversion system for X, Y and Z axis coordinate to radians for radial arm motors, ratio conversion for system using single motor with clutch for various axis control, etc.).

Figure 18A:
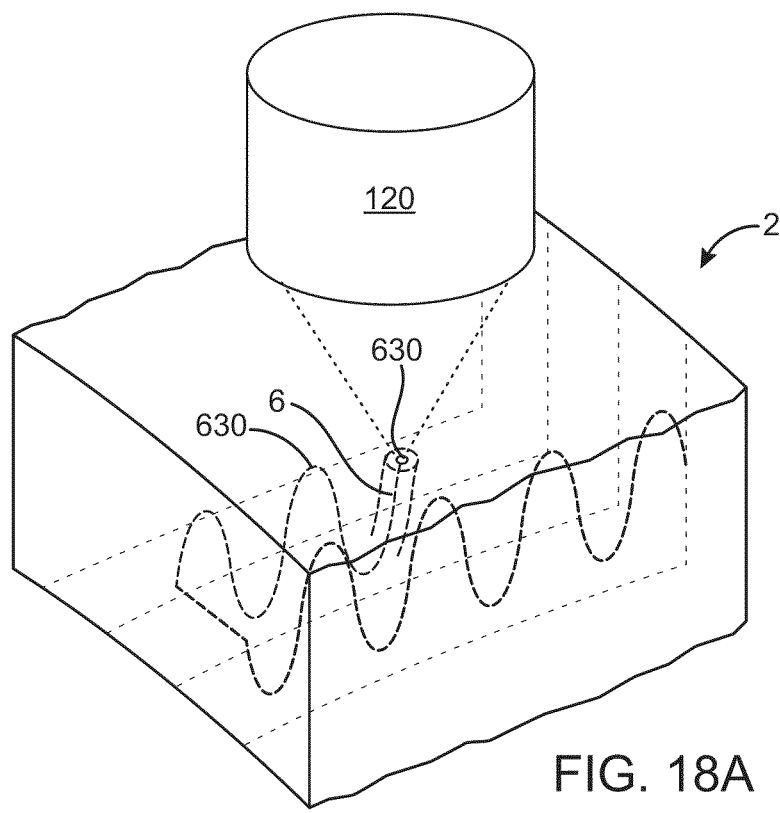
FIGS. 18A-B shows a three dimensional scan in tissue using a transducer within a therapy head driven with the present computer control system
Figure 18B:
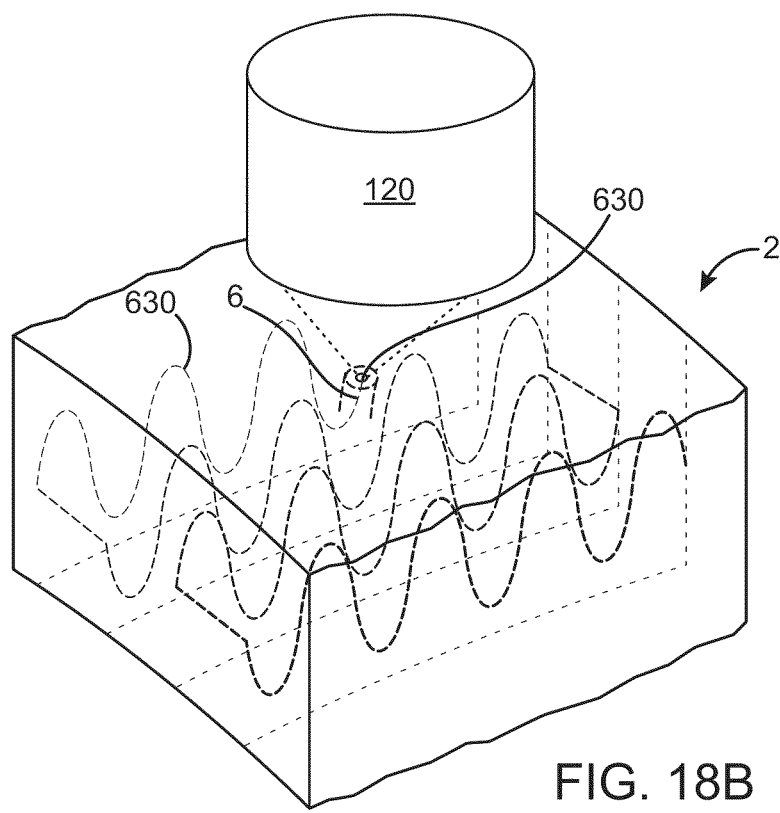

Examples of the three dimensional movement of the transducer within the therapy head 120 are now shown (FIG. 18A-B). Here the transducer moves inside the therapy head according to the three dimensional controller instructions. The therapy head is stationary while the transducer is moved, angled or electronically steered to produce a three dimensional focal path 630c in tissue 2. The focal zone 630 can move in a three dimensional "box" which may correspond to the physical motion limitations of the motor assembly or electronic steering of the therapy head, or it may be a three dimensional shape restriction built into the movement instructions of the controller.

The data store of the controller may contain specific information useful for the treatment of particular body regions, such as large areas of adipose tissue usually found in the abdomen, flank or buttocks, to smaller regions such as around the eye, cheeks or neck. Similarly the data store may contain varying parameters adapted to account for the age, size (weight, BMI or other indicia) of the patient, or gender. By loading the appropriate library information or data table from the data store, the system can automatically treat the volume desired so long as the system therapy head is adapted to treat the desired volume of tissue.

In addition to the data store, the system may have an automated check system so the system will query the therapy head to insure the therapy head is capable of carrying out the parameters required by the controller prior to the initiation of treatment.

Figure 19:
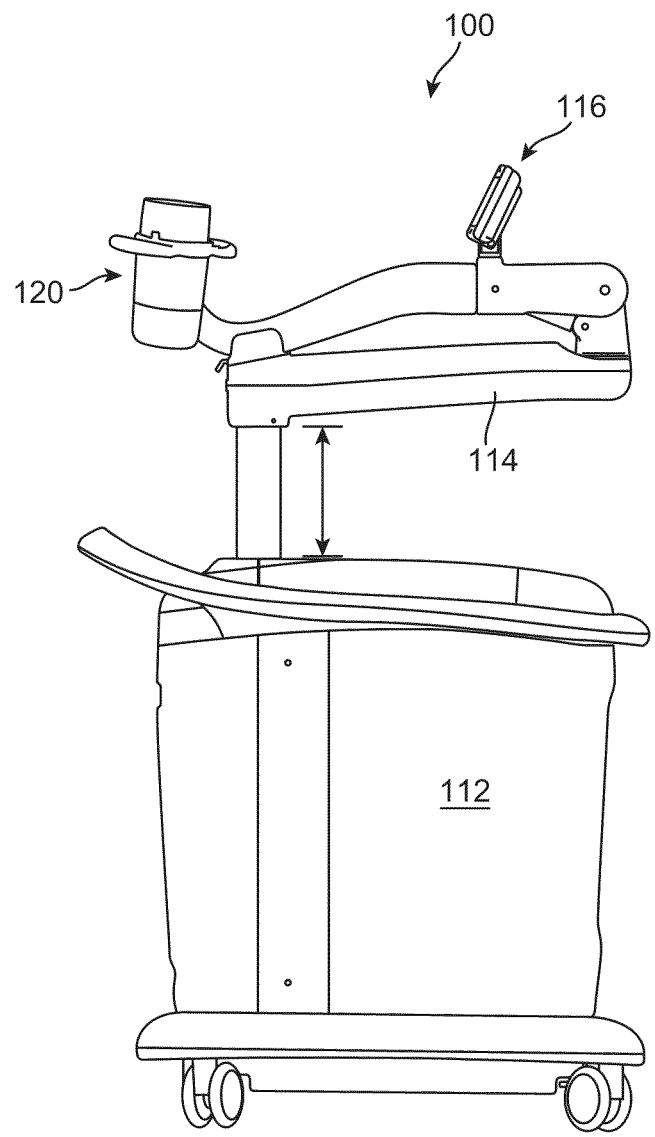
FIG. 19 shows a medical ultrasound therapy system in accordance with an embodiment.

The system and therapy head are now physically described. FIG. 19 shows a medical ultrasound system 100. The medical ultrasound system 100 includes a base unit 112, an articulating arm 114 attached to the base unit, and a user interface device 116 attached to the articulating arm 114. At the distal end of the articulating arm 114 is an ultrasound head 120.

Figure 20:
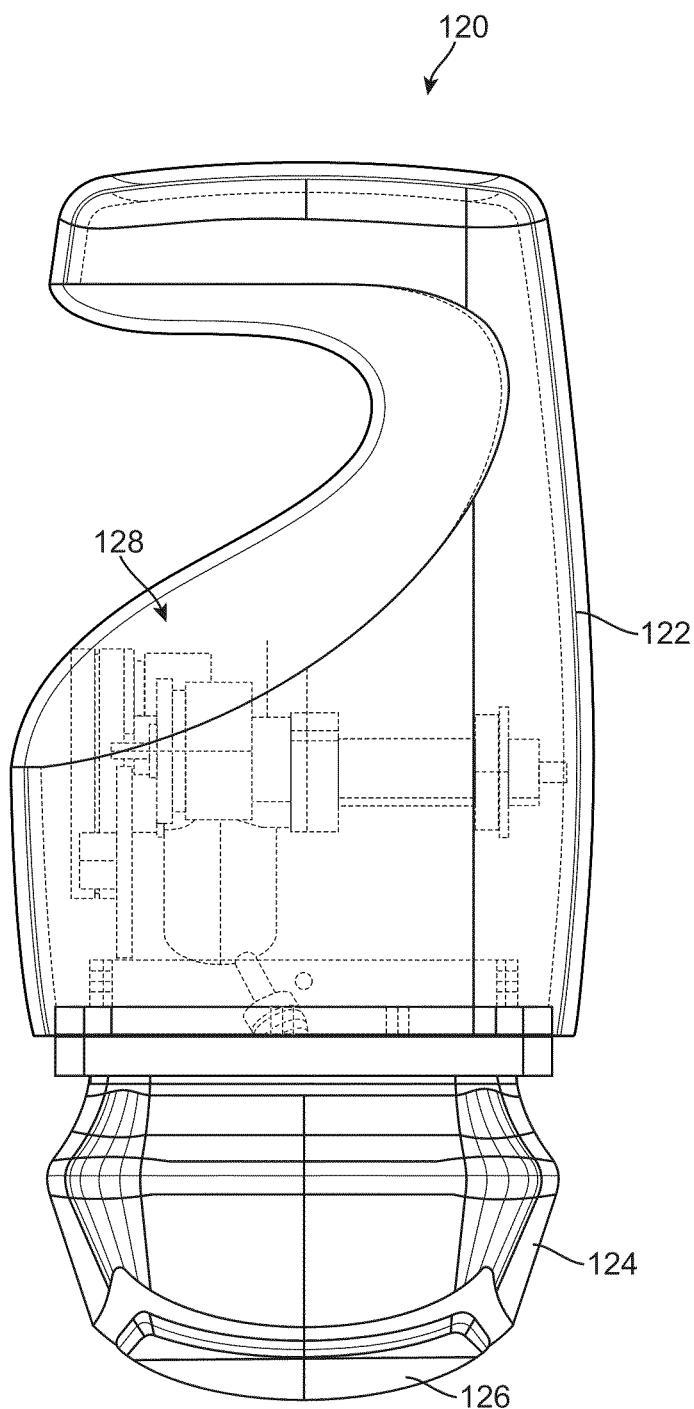
FIG. 20 shows an ultrasound therapy head having an actuation assembly for varying the position/orientation of an ultrasound transducer in accordance with an embodiment.

The exterior of the ultrasound head 120 may be a form factor that can easily handled by an operator. An example of one embodiment is shown in FIG. 20, but the ultrasound head may take many other forms. The ultrasound head 120 may have cables extending from it and going to the base unit 112 through the articulating arm 114, or the cables may optionally be exposed.

As shown in FIG. 20, the ultrasound head 120 includes an upper compartment 122, and a lower compartment 124, or cap. The upper compartment 122 can be dry and house wires, cables, a motor assembly, and/or other features for a transducer, which is mounted in the lower compartment 124. The lower compartment 124 may contain a coupling fluid, such as degassed water, used to transfer ultrasound energy from the transducer to and through a window 126 located near the bottom of the lower compartment. Disposed within the upper compartment 122 is an actuation assembly 128. The actuation assembly 128 provides for control over the position/orientation of the transducer located within the lower compartment 124.

In operation, a technician rolls the medical ultrasound system 100 to adjacent a patient. The technician grasps and moves the ultrasound head 120, with the ultrasound head 120 remaining attached to the articulating arm 114. The ultrasound head 120 may be aligned so that the window 126 can contact with the patient. The user interface device 116 may be operated to generate an appropriate treatment or diagnostic test. During use, the transducer mounted in the lower compartment 124 generates ultrasound energy, which may be used, for example, for the destruction of adipose tissue, as described in U.S. Published Application No. 2006/0122509, incorporated herein by reference. The actuation assembly 128 can be used to provide for simplified treatment procedures. For example, the ultrasound head 120 can be held in stationary contact with the patient while the actuation assembly 128 varies the position/orientation of the ultrasound transducer so as to apply therapeutic treatment to a local region of the patient using a scan pattern that provides a desired coverage, duration, spacing, etc.

Figure 21:
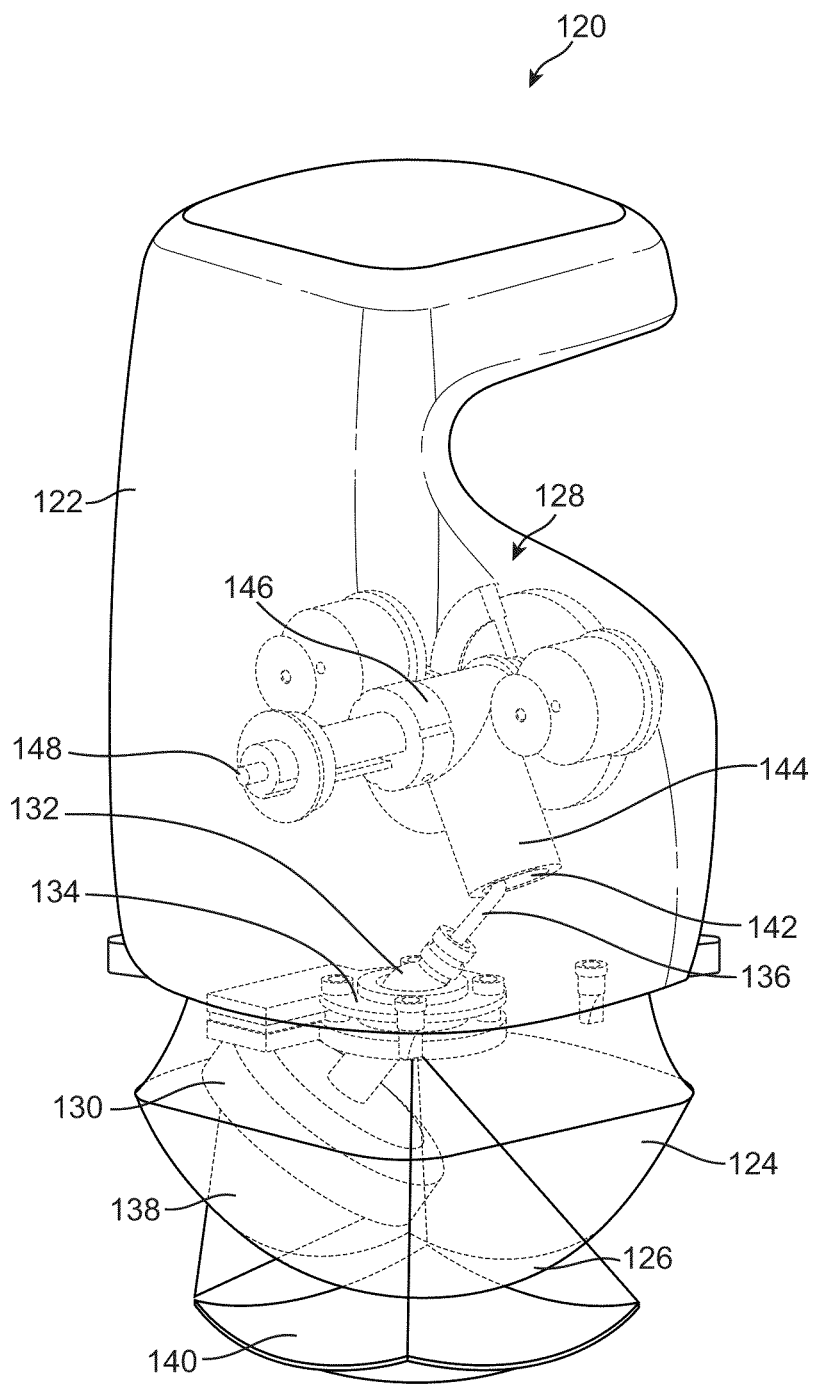
FIG. 21 is a perspective view showing internal assemblies of the ultrasound therapy head of FIG. 19.

FIG. 21 illustrates an embodiment with internal assemblies of the therapy head 120 of FIG. 20. Mounted within the upper compartment 122 is the actuation assembly 128. The actuation assembly 128 is coupled with an ultrasound transducer assembly 130 by way of a control arm 132. The control arm 132 is configured to interface with and pivot within a receptacle 134 that is coupled with a partition that separates the upper compartment 122 from the lower compartment 124. The lower compartment 124 is a sealed assembly that contains a coupling fluid, such as degassed water, that is used to transfer ultrasound energy transmitted by the transducer assembly 130. The receptacle 134 includes at least one fluid seal (e.g., a o-ring seal, a blade seal, etc.) to prevent fluid from entering the upper compartment 122 from the lower compartment 124. The control arm 132 includes a control arm upper end 136 disposed within the upper compartment 122. In the position/orientation shown, the ultrasound transducer assembly 130 is shown as transmitting focused ultrasound energy through the window 126 as illustrated by the ultrasound energy profile 138.

The actuation assembly 128 is operable to move the control arm upper end 136 so as to pivot the control arm 132 within the receptacle 134. The range of motion of the actuation assembly and the control arm 132 produces a coverage area 140 within which focused ultrasound energy can be directed in a controlled fashion (e.g., by using scanning patterns, scanning rates, energy transmission levels, etc.).

Figure 22A:
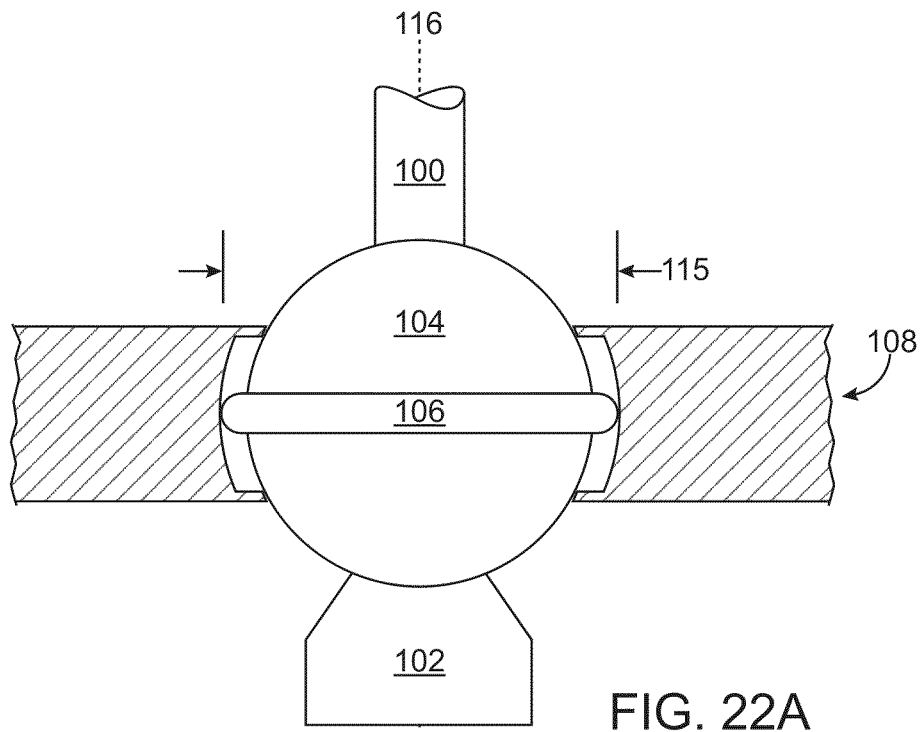
FIGS. 22A-22D are cross-sectional views illustrating details of a coupling between a control arm and a therapy head partition and ranges of motion of the control arm in accordance with an embodiment.
Figure 22B:
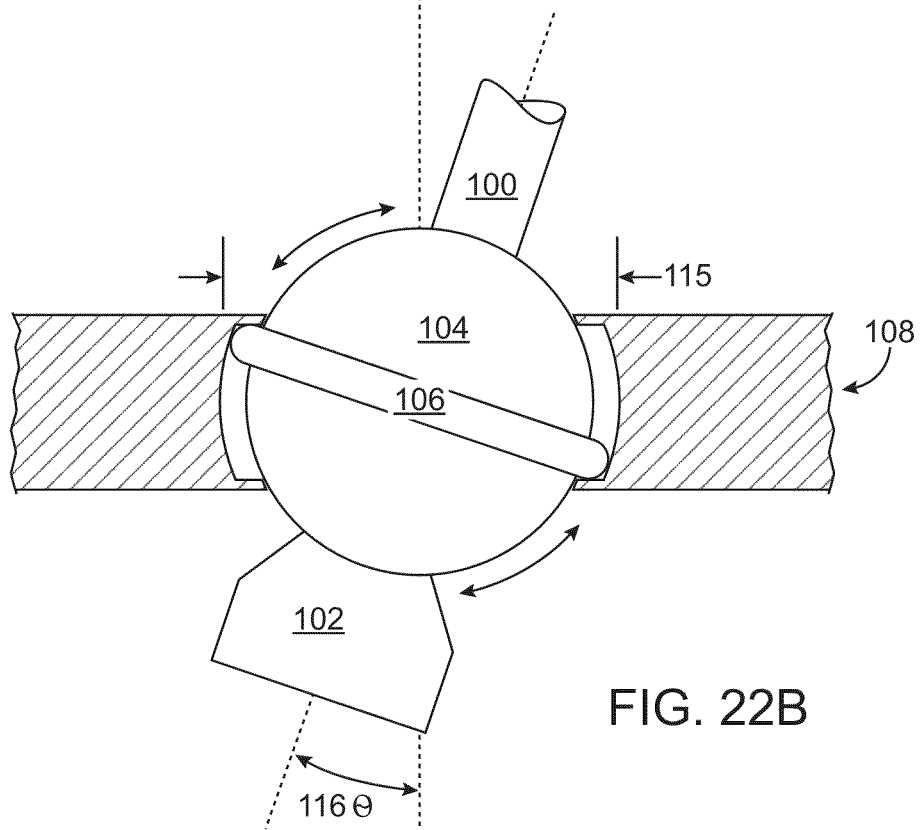
Figure 22C:
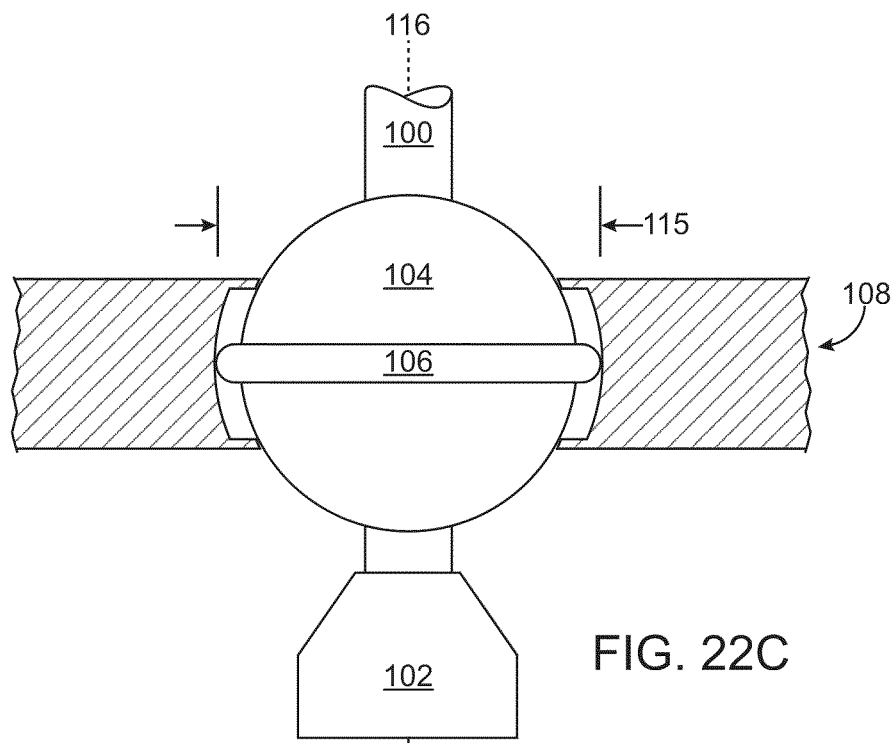
Figure 22D:
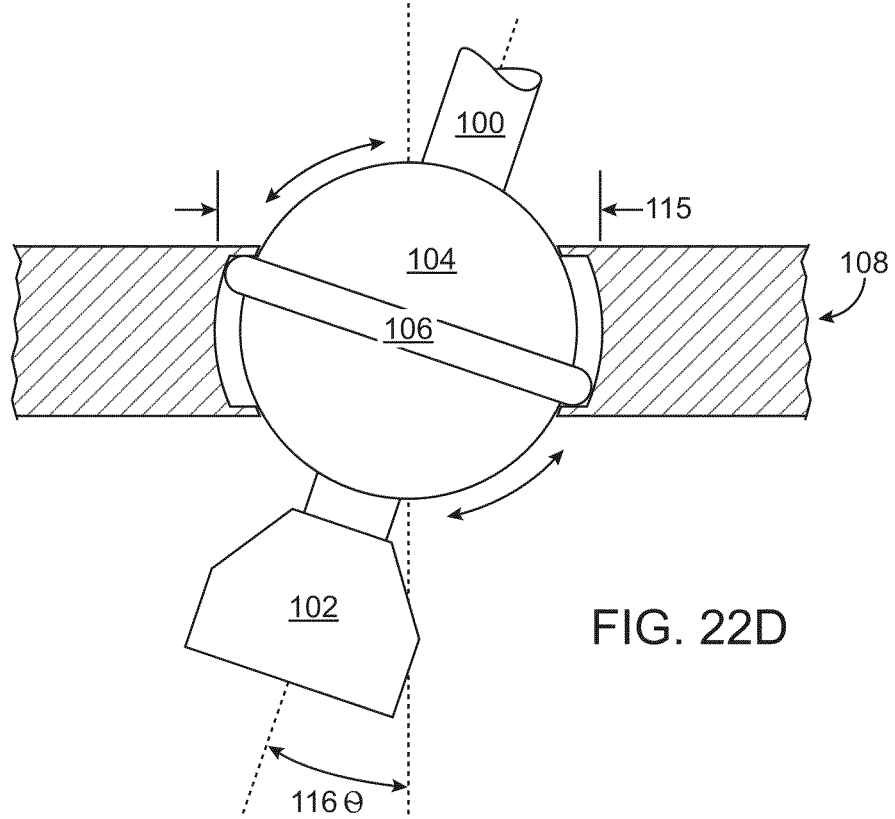

FIG. 22A illustrates the ball-joint 104 in a "neutral" position with the control arm 100 positioned vertically. The ball joint 104 can be constrained by the partition 108 and surrounded by a boot 115. A hard stop or limit mechanism 106 may be provided to prevent the ball joint 104 from moving outside the confines of the boot 115. Electrical control for the transducer 102 can be routed through or along the shaft 100, through the ball joint 104 and can be connected to the transducer 102. FIG. 22B illustrates the ball joint 104 at the limit of one motion with the shaft tilted to one side, and the limit mechanism 106 at the hard stop of the boot 114. FIG. 22C and FIG. 22D show the transducer 102 extended "downward" from the ball joint 104. The motion up and down of the transducer provides an example of Z axis motion of the transducer.

Example tables (FIG. 23-24) provide X, Y and Z axis motion control with trajectory information that can be used in controlling the transducer to produce example scan lines and scan paths as shown in FIGS. 3A-3D, 4A-4C, 5A-5D and FIG. 18. The table data may be tailored to produce particular shapes or define volumes of tissue to be treated. By modifying the data table, the block control can produce a treatment volume corresponding to any shape desired.

Other variations are within the spirit of the present invention. Thus, while the invention is susceptible to various modifications and alternative constructions, certain illustrated embodiments thereof are shown in the drawings and have been described above in detail. It should be understood, however, that there is no intention to limit the invention to the specific form or forms disclosed, but on the contrary, the intention is to cover all modifications, alternative constructions, and equivalents falling within the spirit and scope of the invention, as defined in the appended claims.

The use of the terms "a" and "an" and "the" and similar referents in the context of describing the invention (especially in the context of the following claims) are to be construed to cover both the singular and the plural, unless otherwise indicated herein or clearly contradicted by context. The terms "comprising," "having," "including," and "containing" are to be construed as open-ended terms (i.e., meaning "including, but not limited to,") unless otherwise noted. The term "connected" is to be construed as partly or wholly contained within, attached to, or joined together, even if there is something intervening. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate embodiments of the invention and does not pose a limitation on the scope of the invention unless otherwise claimed. No language in the specification should be construed as indicating any non-claimed element as essential to the practice of the invention.

Preferred embodiments of this invention are described herein, including the best mode known to the inventors for carrying out the invention. Variations of those preferred embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

What is claimed is:

1. A method of modifying adipose tissue using high intensity focused ultrasound (HIFU), the method comprising:
    determining a volume of adipose tissue to be treated;
    identifying a corresponding surface area of skin over said volume of adipose tissue;
    moving a therapy head including a HIFU therapy transducer on said surface area of skin; and transferring the HIFU from the HIFU therapy transducer through a coupling fluid surrounding the HIFU therapy transducer to apply multiple treatments of therapeutic ultrasound energy into said volume of adipose tissue such that a plurality of necrosed tissue cells and denatured collagen fibrils are produced, the multiple treatments occurring at least at two different depths.

2. A method of reducing adipose tissue volume in a patient using high intensity focused ultrasound, the method comprising:

determining a volume of adipose tissue to be treated;
identifying a corresponding surface area of skin over said volume of adipose tissue; and
transferring the high intensity focused ultrasound from a transducer through a coupling fluid surrounding the transducer to apply multiple treatments of high intensity focused ultrasound energy to said area in a manner sufficient to induce the gradual destruction of said adipose tissue and denaturing of collagen fibrils, the energy flux of the multiple treatments being at least 35 J/cm$^2$, and the multiple treatments occurring at least at two different depths.

3. A medical ultrasound therapy system for treating a volume of adipose tissue, comprising:

a therapy head including a first chamber, a coupling fluid in the first chamber, and at least one high intensity focused ultrasound transducer surrounded by the coupling fluid in the first chamber, the at least one high intensity focused ultrasound transducer configured to emit high intensity focused ultrasound from the at least one high intensity focused ultrasound transducer through the coupling fluid to the volume of adipose tissue; and
a controller comprising:
a data store storing information about a three dimensional treatment profile for the therapy head; and
a processor coupled to the data store, the processor generating a three dimensional treatment cycle for the therapy head in accordance with the information, the three dimensional treatment cycle including treatments by the therapy head at a plurality of different depths.

4. The system of claim 3, wherein the therapy head comprises:

an enclosure with a partition, the partition defining the first chamber and a second chamber within the enclosure; and
a motor assembly within the second chamber,
wherein the high intensity focused ultrasound transducer is movable within the first chamber through motor commands provided to the motor assembly from the controller.

5. The system of claim 3, wherein the data store further comprises information stored in library tables.

6. The system of claim 3, wherein the data store further comprises profile data particular to various anatomical regions of adipose tissue.

7. The system of claim 6, wherein the profile data is adapted for gender variations.

8. The system of claim 3, wherein the therapy head is adapted for various anatomical regions of adipose tissue.

9. The system of claim 3, wherein the controller is adapted to promote an effect of necrosis of adipose tissue.

10. The system of claim 3, wherein the controller is adapted to promote an effect of denaturing collagen fibrils.

11. A medical ultrasound therapy system for treating a volume of adipose tissue, comprising:

a therapy head including a first chamber, a coupling fluid in the first chamber, and at least one high intensity focused ultrasound transducer surrounded by the coupling fluid in the first chamber, the at least one high intensity focused ultrasound transducer configured to emit high intensity focused ultrasound from the at least one high intensity focused ultrasound transducer through the coupling fluid to the volume of adipose tissue; and
a controller for generating a three dimensional treatment plan for the therapy head, the controller comprising:
a data access component for accessing data defining a three dimensional treatment profile for a treatment of a defined region of a patient, the treatment profile including information about treatments to be conducted at a plurality of different depths; and
a treatment plan component for generating a treatment plan based upon the treatment profile, the treatment plan including treatments defined for the therapy head at the plurality of different depths in accordance with the information.

12. The system of claim 11, wherein the therapy head comprises:

an enclosure with a partition, the partition defining the first chamber and a second chamber within the enclosure; and
a motor assembly within the second chamber,
wherein the high intensity focused ultrasound transducer is movable within the first chamber through motor commands provided to the motor assembly from the controller.

13. The system of claim 11, wherein the data store further comprises information stored in library tables.

14. The system of claim 11, wherein the data store further comprises profile data particular to various anatomical regions of adipose tissue.

15. The system of claim 14, wherein the profile data is adapted for gender variations.

16. The system of claim 11, wherein the therapy head is adapted for various anatomical regions of adipose tissue.

17. The system of claim 11, wherein the controller is adapted to promote an effect of necrosis of adipose tissue.

18. The system of claim 11, wherein the controller is adapted to promote an effect of denaturing collagen fibrils.

19. A method for treating a patient with high intensity focused ultrasound, the method comprising:

positioning a therapy head having at least one high intensity focused ultrasound transducer against a first location on a patient; and
using an automated process:
while at the first location, transferring the high intensity focused ultrasound from the at least one high intensity focused ultrasound transducer through a coupling fluid to ablate the tissue at a first depth; and
while at the first location, transferring the high intensity focused ultrasound from the at least one high intensity focused ultrasound transducer through the coupling fluid in the therapy head to ablate tissue at a second depth.

20. The method of claim 19, wherein the automated process comprises:

accessing information about a plurality of depths profile for the therapy head; and
generating a multi-depth treatment cycle for the therapy head in accordance with the information, the multi-depth treatment cycle including treatments by the therapy head at the plurality of depths.

21. The method of claim 20, wherein the information is stored in library tables.

22. The method of claim 20, wherein the information comprises profile data particular to various anatomical regions of adipose tissue.

23. The method of claim 19, wherein the therapy head comprises:
- an enclosure with a partition, the partition defining the first chamber and a second chamber within the enclosure; and
- a motor assembly within the second chamber,
- wherein the high intensity focused ultrasound transducer is movable within the first chamber through motor command provided to the motor assembly from the controller; and
- wherein the automated process comprises the ultrasound transducer moving with the first chamber through motor command.

24. The method of claim 23, wherein the profile data is adapted for gender variations.

25. The method of claim 23, wherein depth variation is provided by varying the focus of the ultrasound transducer.

26. The method of claim 19, wherein ablating tissue comprises promoting an effect of necrosis of adipose tissue.

27. The method of claim 19, wherein ablating tissue comprises promoting promote an effect of denaturing collagen fibrils.

28. A medical ultrasound therapy system, comprising:
- a therapy head including a first chamber, a coupling fluid in the first chamber, and at least one high intensity focused ultrasound transducer surrounded by the coupling fluid in the first chamber, the at least one high intensity focused ultrasound transducer configured to emit high intensity focused ultrasound from the at least one high intensity focused ultrasound transducer through the coupling fluid to the volume of adipose tissue; and
- a controller comprising:
  - a data store having stored thereon a data structure, the data structure comprising a tissue ablation treatment routine comprising a first data field containing data representing a routine for first ablation of tissue at a first depth in accordance with the routine and a second data field representing a routine for second ablation of tissue at a second depth in accordance with the routine; and
  - a processor coupled to the data store, the processor accessing the data structure and instructing the therapy head to perform the routine in an automated process and including the first ablation and the second ablation.

29. The system of claim 28, wherein the therapy head comprises:
- an enclosure with a partition, the partition defining the first chamber and a second chamber within the enclosure; and
- a motor assembly within the second chamber,
- wherein the high intensity focused ultrasound transducer is movable within the first chamber through motor command provided to the motor assembly from the controller.

30. The system of claim 28, wherein the data store further comprises information stored in library tables.

31. The system of claim 28, wherein the data store further comprises profile data particular to various anatomical regions of adipose tissue.

32. The system of claim 31, wherein the profile data is adapted for gender variations.

33. The system of claim 28, wherein the therapy head is adapted for various anatomical regions of adipose tissue.

34. The system of claim 28, wherein the controller is adapted to promote an effect of necrosis of adipose tissue.

35. The system of claim 28, wherein the controller is adapted to promote an effect of denaturing collagen fibrils.

* * * * *

UNITED STATES PATENT AND TRADEMARK OFFICE
CERTIFICATE OF CORRECTION

PATENT NO.        : 9,623,267 B2
APPLICATION NO.   : 12/717818
DATED             : April 18, 2017
INVENTOR(S)       : Ulric et al.

Page 1 of 1

It is certified that error appears in the above-identified patent and that said Letters Patent is hereby corrected as shown below:

In the Claims

Column 19, Claim 27, Line 25, after "promoting" delete "promote"

Signed and Sealed this
Thirtieth Day of May, 2017

Michelle K. Lee
*Director of the United States Patent and Trademark Office*